(12) United States Patent
Srivastava et al.

(10) Patent No.: US 11,286,241 B2
(45) Date of Patent: Mar. 29, 2022

(54) COMPOSITIONS AND METHODS FOR TREATING CANCER

(71) Applicant: GLAX LLC, Wilmington, DE (US)

(72) Inventors: Rakesh K Srivastava, New Orleans, LA (US); Sharmila Shankar, New Orleans, LA (US); Sushant Kumar Shrivastava, Benares (IN); Prabhash Nath Tripathi, Benares (IN); Pavan Srivastava, Benares (IN)

(73) Assignee: GLAX LLC, Wilmington, DE (US)

( * ) Notice: Subject to any disclaimer, the term of this patent is extended or adjusted under 35 U.S.C. 154(b) by 197 days.

(21) Appl. No.: 16/565,330

(22) Filed: Sep. 9, 2019

(65) Prior Publication Data
US 2020/0087267 A1   Mar. 19, 2020

Related U.S. Application Data

(60) Provisional application No. 62/728,439, filed on Sep. 7, 2018.

(51) Int. Cl.
| | | |
|---|---|---|
| C07D 263/57 | (2006.01) | |
| C07D 413/12 | (2006.01) | |
| A61K 31/423 | (2006.01) | |
| A61P 35/00 | (2006.01) | |
| A61K 31/167 | (2006.01) | |
| A61K 31/53 | (2006.01) | |

(52) U.S. Cl.
CPC .......... *C07D 263/57* (2013.01); *C07D 413/12* (2013.01); *A61K 31/167* (2013.01); *A61K 31/53* (2013.01)

(58) Field of Classification Search
CPC .. C07D 263/57; C07D 413/12; A61K 31/423; A61P 35/00
USPC .......................................... 548/224; 514/375
See application file for complete search history.

(56) References Cited

FOREIGN PATENT DOCUMENTS

WO    WO-9506469 A1 *  3/1995    ............ A61K 31/42

OTHER PUBLICATIONS

Hajipour, A., Z. Khorsandi, M. Mortazavi and H. Farrokhpour, "Green, efficient and large-scale synthesis of benzimidazoles, benzoxazoles and benzothiazoles derivatives using ligand-free cobalt-nanoparticles: as potential anti-estrogen breast cancer agents . . . " RSC Adv., 2015, 5, pp. 107822-107828. (Year: 2015).*
Franken Dick, P., F. Lange Coelho, F. Severo Rodembusch and L. Franciscato Campo, "Amphiphilic ESIPT benzoxazole derivatives as prospective fluorescent membrane probes", Tetrahedron Letters 55 (2014), pp. 3024-3029. (Year: 2014).*

* cited by examiner

*Primary Examiner* — Joseph R Kosack
*Assistant Examiner* — Sagar Patel

(57) ABSTRACT

This invention is directed to compositions and methods for treating cancer in a patient.

20 Claims, 22 Drawing Sheets

Design Considerations

- β-Amino alcohol : important pharmacophore in the various anticancer compounds.

- Benzoxazole: various derivatives are inhibitor of hedgehog signaling pathway.

- Designed compound: we had linked the benzoxazole with 1,3-bis(phenylamino)propan-2-ol having active β-Amino alcohol active moieties

FIG. 6

| Protein | Ligand | Glide Score (Kcal/mole) | Interacting Residue | Bond Type |
|---|---|---|---|---|
| 4JKV | LY2940680 (Known Inhibitor) | -11.602 | Asn-521,Arg-400,Ile-234,Ser-387,Val-386,Leu-515,Pro-513,Met-230,Asp-473,Phe-222,Leu-221,Trp-480,Phe-484,Lys-395,Glu-481,Met-301,Leu-303,Tyr-394,Asp-384,Gln-477,Gln-518,His-470,Trp-281,Ile-389,Phe-391,Met-525,Leu-522 | 1 Hydrogen bonding, 3n interaction(Trp-281,His-470,Phe-484,Arg-400, other hydrophobic interaction |
| | Compound 8 | -10.66 | Leu-303,Met-301,Val-386,Asp-384,Asp-473,His-470,Arg-400,Leu-325,Met-525,Asn-521,Trp-281,Ile-389, Ser-387,Phe-391,Leu-522,Tyr-394, Phe-222,Leu-221,Pro-513,Phe-484,Glu-481,Lys-395 | 3 Hydrogen bonding (Gln-518,Arg-400, & Tyr-394 ),4n interaction(Trp-281,Phe-281,Phe-391,Phe-484,His-470), other hydrophobic interaction |

FIG. 7

| Compound code | AChE IC$_{50}$ (µM) ± SEM | BChE IC$_{50}$ (µM) ± SEM | [a]Selectivity Index |
|---|---|---|---|
| SST-7 / GL-701 | 0.363 ± 0.017 | 2.29 ± 0.09 | 6.3 ± 0.4 |
| Donepezil * | 0.04 ± 0.01 | 15.24 ± 0.88 | 381 ± 6.33 |

FIG. 19

COMPOSITIONS AND METHODS FOR TREATING CANCER

This application claims priority from U.S. Provisional Application No. 62/728,439 filed on Sep. 7, 2018.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to compositions and methods for treating cancer in a patient.

BACKGROUND OF THE INVENTION

Activation of hedgehog pathway plays a role in embryonic development. The pathway is equally important during vertebrate embryonic development and is therefore of interest in evolutionary developmental biology. In knockout mice lacking components of the pathway, the brain, skeleton, musculature, gastrointestinal tract and lungs fail to develop correctly. Recent studies indicate a role for Hedgehog signaling in regulating adult stem cells involved in maintenance and regeneration of adult tissues. Disruption of hedgehog signaling during embryonic development, through either deleterious mutation or consumption of teratogens by the gestating mother, can lead to severe developmental abnormalities.

SUMMARY OF THE INVENTION

Aspects of the invention are directed towards a compound of Formula I:

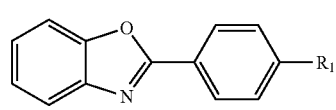

(I)

In embodiments, $R_1$ comprises

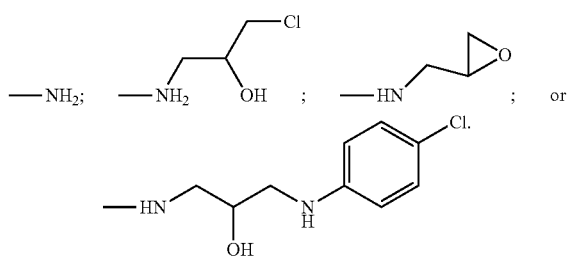

In embodiments, the compound comprises:

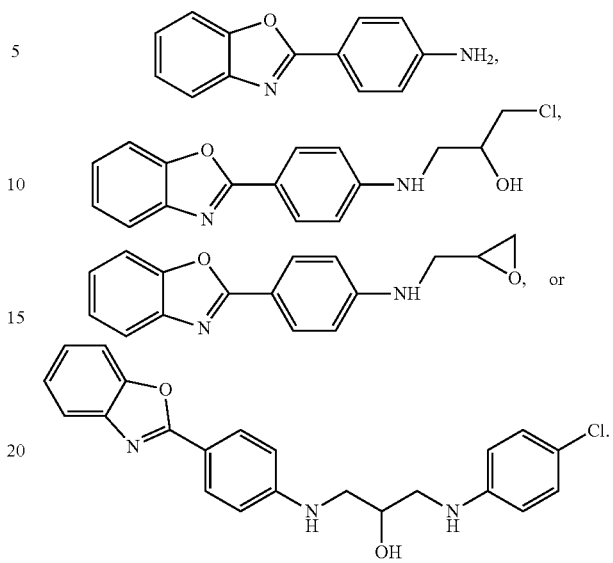

In embodiments, the compound comprises the spectral peaks according to FIG. 3, FIG. 4, FIG. 5 and/or FIG. 6.

Aspects of the invention are also directed towards a pharmaceutical composition comprising a compound of Formula I and a pharmaceutically acceptable carrier.

In embodiments, the pharmaceutical composition further comprises a second active agent, for example PI3K/Akt inhibitor (PF05212384) or histone deacetylase inhibitor SAHA. In embodiments, the second active agent is an anticancer agent.

Aspects of the invention are still further directed towards a method of treating a patient afflicted with cancer. In embodiments, the method comprises administering to the patient an effective amount of a compound of Formula I and a pharmaceutically acceptable carrier. Non-limiting examples of cancers that can be treated by the invention comprise glioma, glioblastoma, liver cancer, colorectal cancer, stomach cancer, brain cancer, prostate cancer, breast cancer, ovarian cancer, testicular cancer, gallbladder cancer, mesothelioma, kidney cancer, sarcoma, melanoma, retinoblastoma, skin cancer, head and neck cancer, thyroid cancer, vaginal cancer, leukemia, lymphoma, lung cancer, and pancreatic cancer.

In embodiments, the compound is administered in a single dose.

In embodiments, the compound is administered continuously.

In embodiments, the compound is administered at intervals of about 4 hours, 12 hours, or 24 hours.

In embodiments, the compound is administered orally, parentally, transdermally, or nasally.

Aspects of the invention are also directed towards a method of reducing cell viability. In embodiments, the method comprises contacting a cell with an effective amount of a compound of Formula I and a pharmaceutically acceptable carrier.

Further, aspects of the invention are directed towards methods of inducing apoptosis of a cell, methods of inhibiting cell proliferation, methods of regulating epithelial-mesenchymal transition (EMT), and/or methods of inhibiting tumor growth. In embodiments, the method comprises contacting a cell with an effective amount of a compound of Formula I and a pharmaceutically acceptable carrier. In embodiments, the compound is administered to a subject prior to contacting. In embodiments, the compound contacts and/or interacts with the SMO receptor, such as at the interacting residues of FIG. 7, or any combination thereof.

Non-limiting examples of such cells comprise cancer cells, such as a glioma cancer cell, glioblastoma cancer cell, liver cancer cell, colorectal cancer cell, stomach cancer cell, brain cancer cell, prostate cancer cell, breast cancer cell, ovarian cancer cell, testicular cancer cell, gallbladder cancer cell, mesothelioma cancer cell, kidney cancer cell, sarcoma cancer cell, melanoma cancer cell, retinoblastoma cancer cell, skin cancer cell, head and neck cancer cell, thyroid cancer cell, vaginal cancer cell, leukemia cancer cell, lymphoma cancer cell, lung cancer cell, and pancreatic cancer cell.

Aspects of the invention are further directed towards a medical kit suitable for the treatment of cancer. In embodiments, the kit comprises printed instructions for administering a compound of Formula I to a subject afflicted with a cancer; or a pharmaceutical composition comprising a compound of Formula I and a pharmaceutically acceptable carrier.

Other objects and advantages of this invention will become readily apparent from the ensuing description.

BRIEF DESCRIPTION OF THE FIGURES

FIG. 7 shows molecular docking analysis on SMO receptor active transmembrane binding site of standard drug (LY2940680) and Compound 8 on PDB:4JKV.

FIG. 19 shows IC$_{50}$ values of synthesized derivatives of SST-7/GL-701.

DETAILED DESCRIPTION OF THE INVENTION

Abbreviations and Definitions

Figure 1:
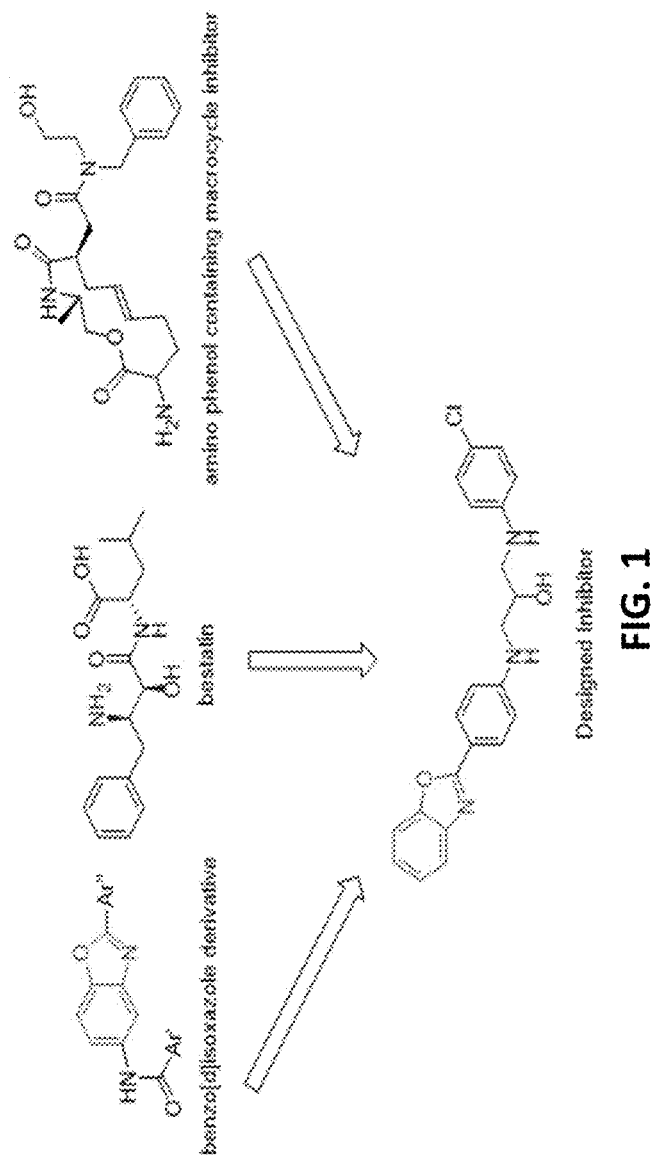
FIG. 1 shows the designing of an embodiment of the invention, a novel inhibitor of the Hedgehog signaling pathway.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

Hedgehog Pathway

Aspects of the invention are directed towards compositions and methods for treating and/or preventing in a patient a disease where the hedgehog pathway is aberrantly or abruptly activated. In embodiments, the disease is a cancer.

Activation of hedgehog pathway plays a role in embryonic development. It has been linked to several diseases such as neurological disorders and various cancers. The pathway is equally important during vertebrate embryonic development and is therefore of interest in evolutionary developmental biology. In knockout mice lacking components of the pathway, the brain, skeleton, musculature, gastrointestinal tract and lungs fail to develop correctly. Recent studies indicate a role for Hedgehog signaling in regulating adult stem cells involved in maintenance and regeneration of adult tissues. Disruption of hedgehog signaling during embryonic development, through either deleterious mutation or consumption of teratogens by the gestating mother, can lead to severe developmental abnormalities.

Activation of the hedgehog pathway is implicated in the development of cancers in various organs, including brain, lung, mammary gland, prostate and skin. Activation of the Hedgehog pathway leads to an increase in Snail protein expression and a decrease in E-cadherin and tight junctions. Hedgehog signaling pathway regulates angiogenesis, epithelial-mesenchymal transition and metastasis. Loss-of-function mutations in Patched and activating mutations in Smoothened have been identified in patients. Abnormal activation of the pathway leads to development of disease through transformation of adult stem cells into cancer stem cells that give rise to the tumor. Therefore, without wishing to be bound by theory, specific inhibitors of hedgehog signaling, such as those described herein, can provide an efficient therapy for a wide range of malignancies.

Embodiments described herein address unmet needs in the field, as existing drugs are not very effective at treating cancer, and existing treatments can result in drug resistance and cancer relapse. For example, embodiments described herein can not only inhibit cancer cells, but also inhibit cancer stem cells, which cause cancer initiation, progression, drug resistance and relapse.

Anti-Cancer Compounds and Pharmaceutical Compositions

Aspects of the invention are further directed towards compounds for the prevention and/or treatment of a disease associated with Hedgehog pathway, such as cancer, and pharmaceutical compositions comprising the same.

In embodiments, the compound comprises a compound of Formula I:

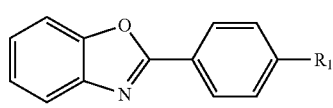

(I)

In embodiments, R1 can comprise

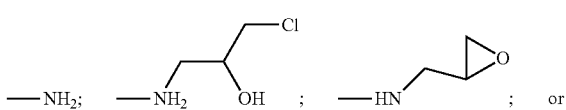

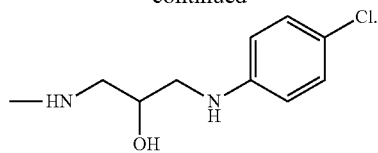

In embodiments, the compound comprises a compound of Formula II:

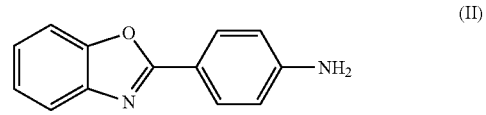 [SMILES: Nc1ccc(-c2nc3ccccc3o2)cc1]

(II)

In embodiments, the compound comprises a compound of Formula III:

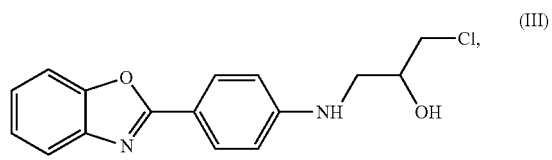 [SMILES: OC(CCl)CNc1ccc(-c2nc3ccccc3o2)cc1]

(III)

In embodiments, the compound comprises a compound of Formula IV:

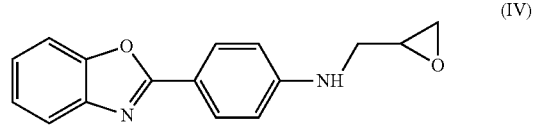 [SMILES: c1ccc2oc(-c3ccc(NCC4CO4)cc3)nc2c1]

(IV)

In embodiments, the compound comprises a compound of Formula V:

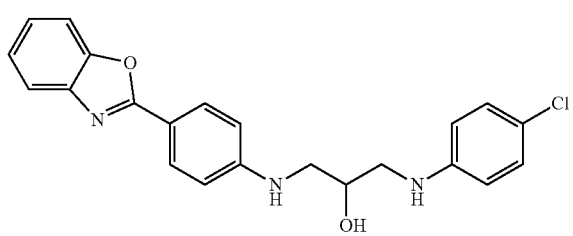

(V)

Figure 2:
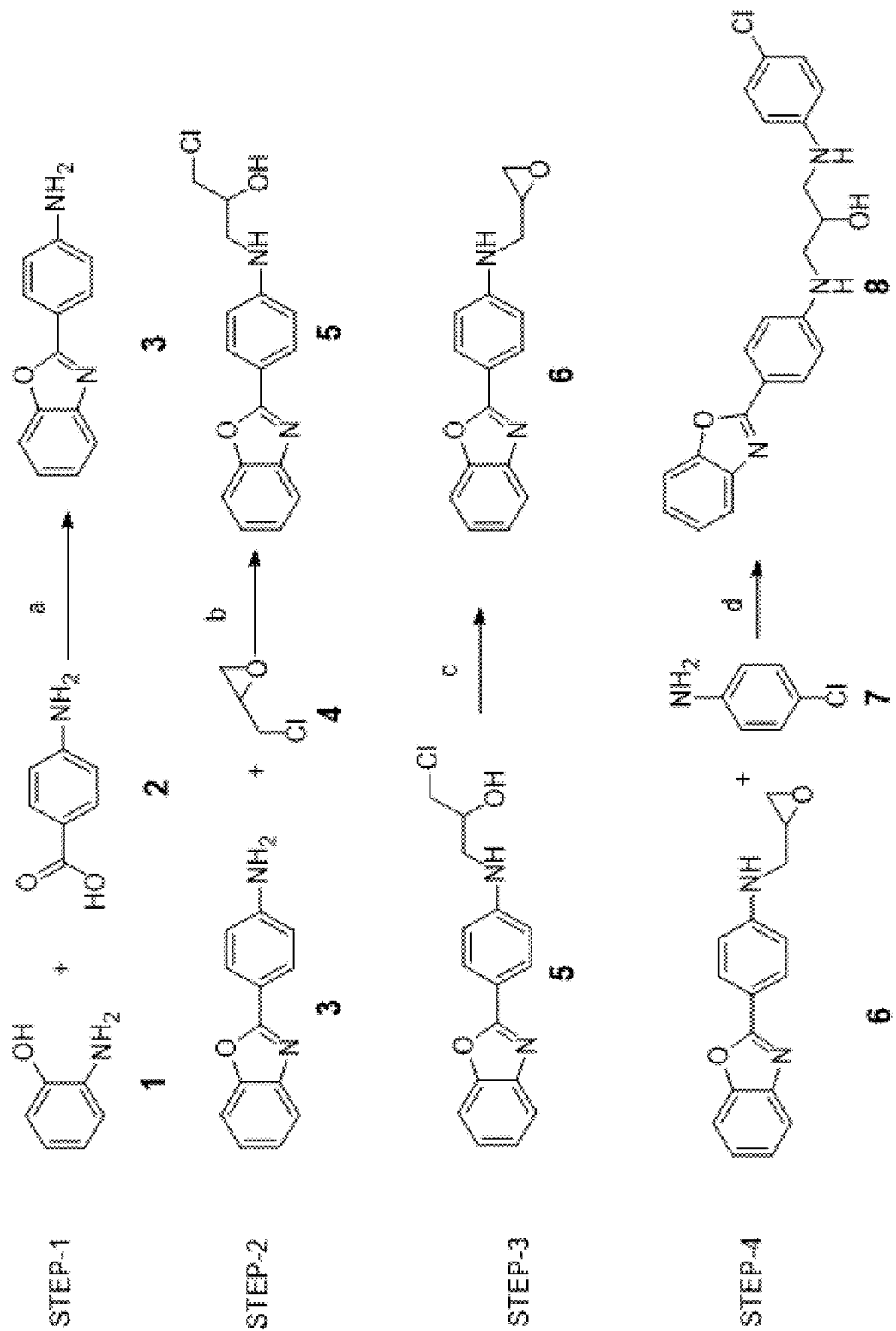
FIG. 2 shows the synthetic scheme of compound 8. Reagents and conditions: (a) polyphosphoric acid, 170-180° C., 8 h; (b) Silica gel (60-120 mesh, 50% w/w), 72 h; (c) KOH, diethylether, 24 h; (d) ethanol, 60-65° C., 5 h.

Referring to FIG. 1 and FIG. 2, for example, embodiments can be synthesized by linking the benzoxazole with 1,3-bis(phenylamino)propan-2-ol having active β-Amino alcohol active moieties (see Example 1). In embodiments, Formula I can be referred to as compound 8 or SST7 or GL-701.

Figure 3:
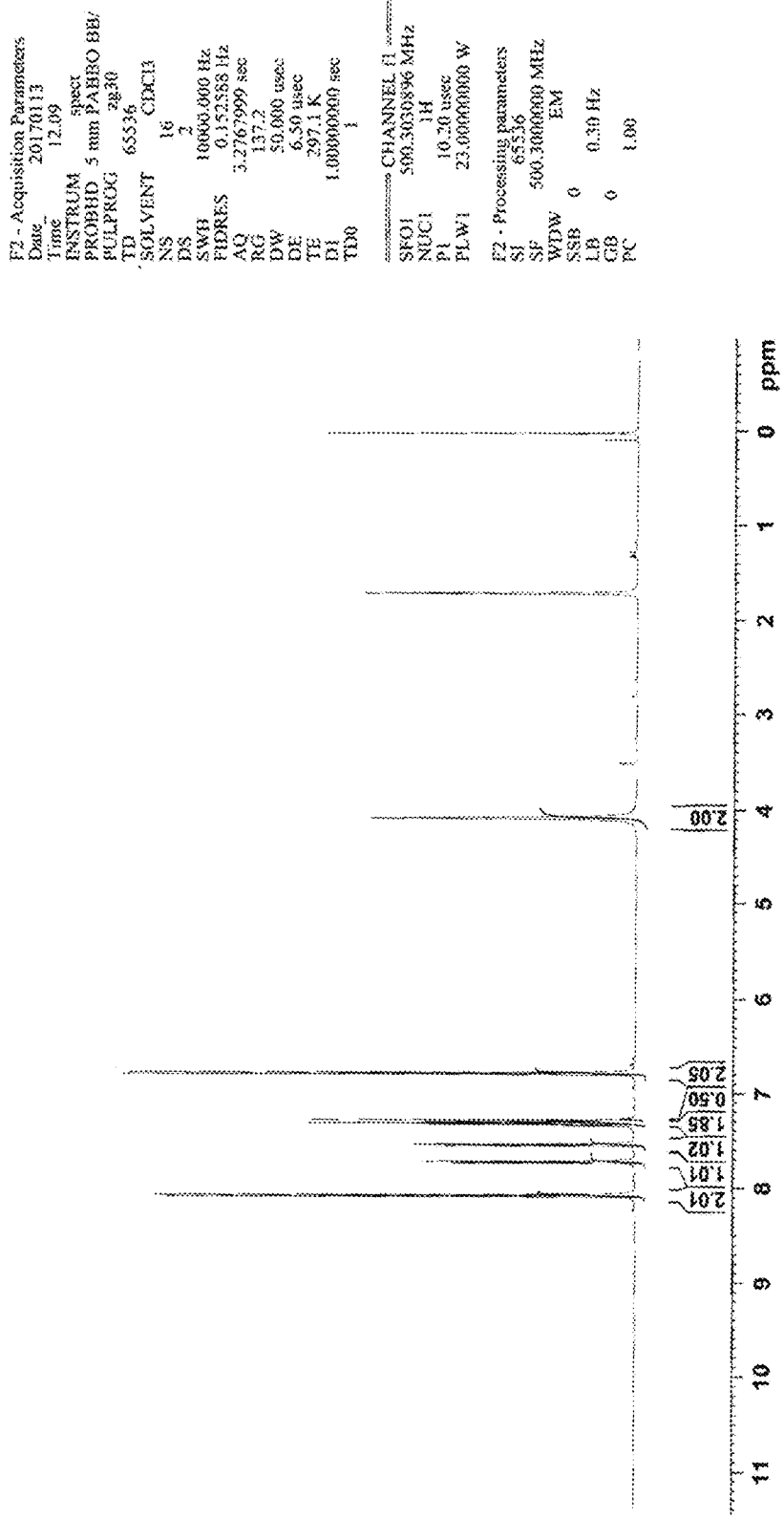
FIG. 3 shows the $^1$H NMR spectra of compound 3.
Figure 4:
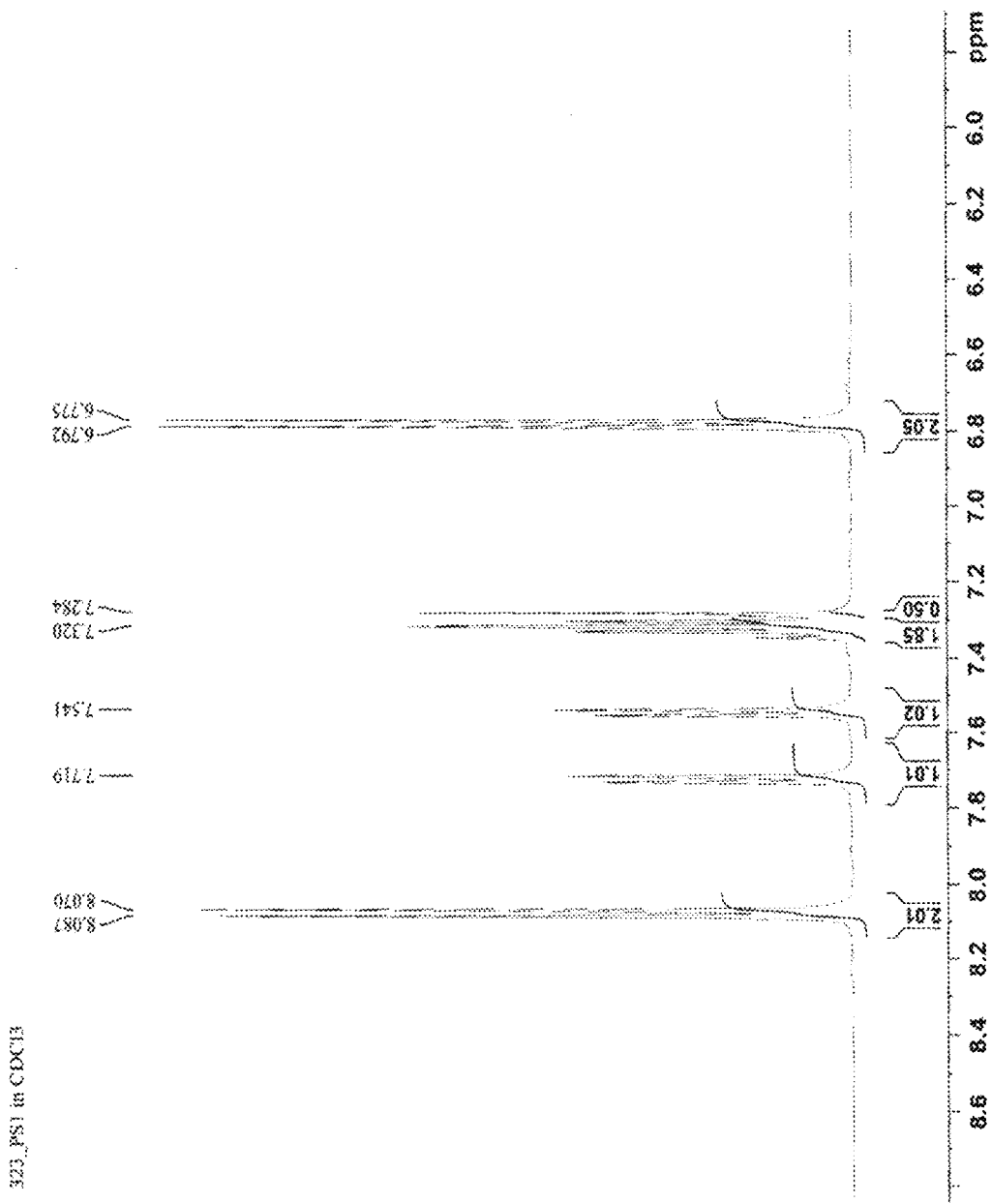
FIG. 4 shows the $^1$H NMR spectra of compound 3.
Figure 5:
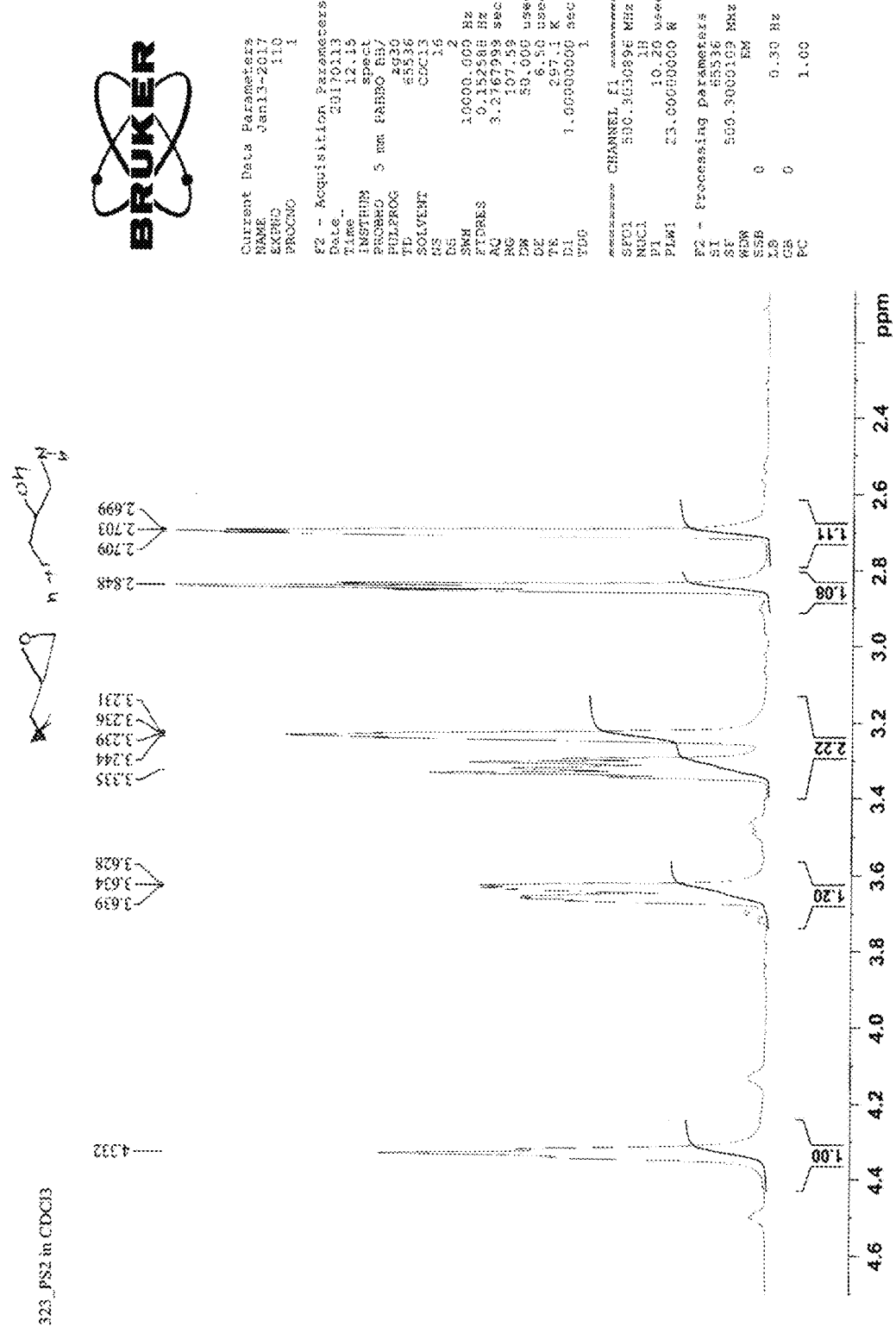
FIG. 5 shows the $^1$H NMR spectra of compound 6.
Figure 6:
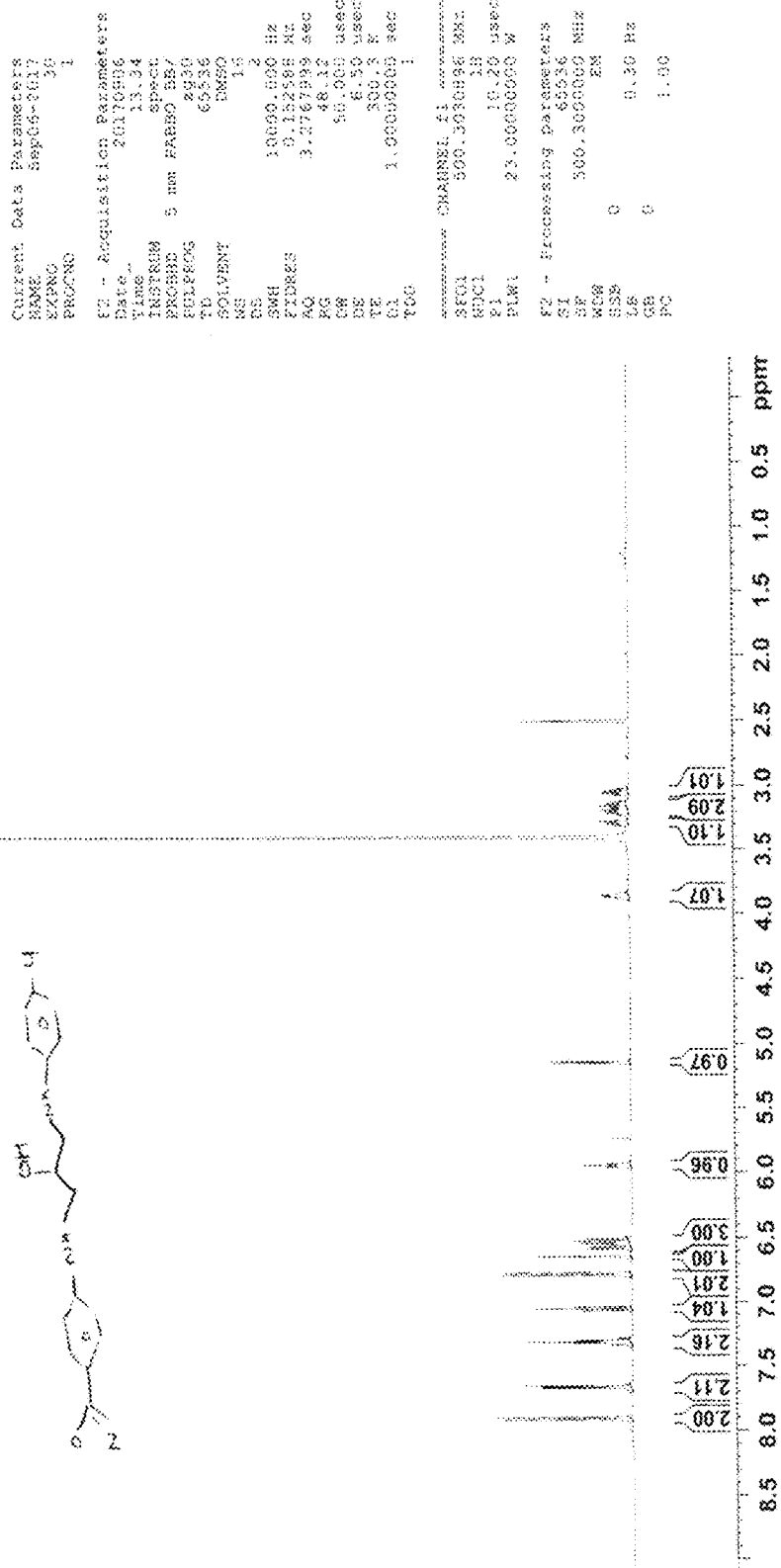
FIG. 6 shows the $^1$H NMR spectra of compound 8.

In embodiments, the compound can comprise the compound comprising the spectral peaks according to FIG. 3, FIG. 4, FIG. 5, and/or FIG. 6. Referring to FIG. 3 and FIG. 4, for example, the compound can be referred to as compound 3 (i.e., Formula II). Referring to FIG. 5, the compound can be referred to as compound 6 (i.e., Formula IV).

Referring to FIG. 6, for example, the compound can be referred to as compound 8 (i.e., Formula V).

In embodiments, the compounds can be synthesized according to the following synthetic scheme:

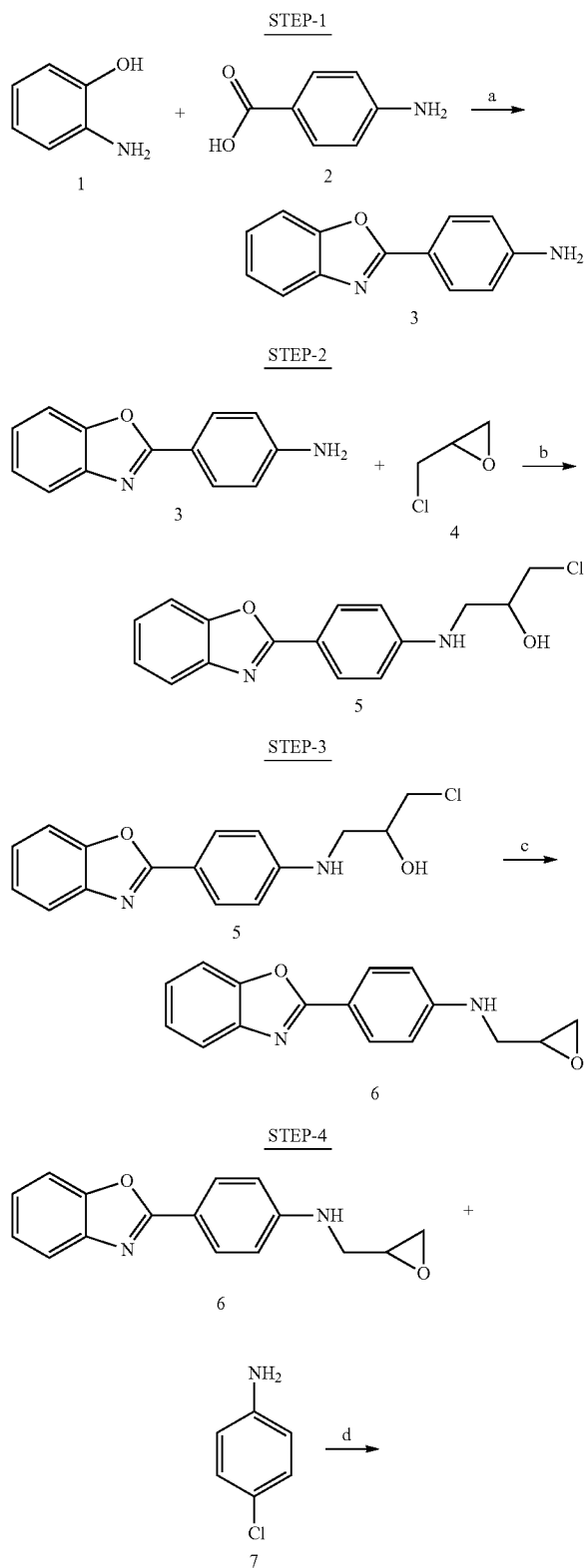

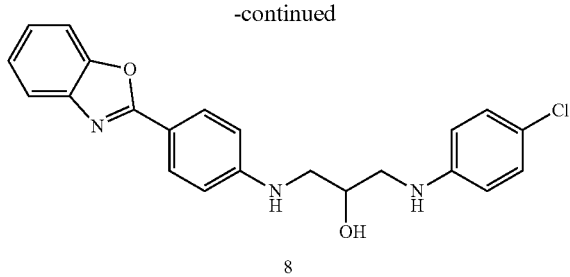

In embodiments, the compound can contact and/or interact with the SMO receptor. Referring to FIG. 7, the compound can contact and/or interact with the SMO receptor at specific interacting residues of SMO receptor. For example, FIG. 10 and FIG. 11 indicate the protein-ligand contacts of a compound of Formula I for 10 ns simulation run on 4JKV.

Pharmaceutical compositions for the treatment of a disease associated with the Hedgehog pathway can comprise at least one compound as described herein, such as a compound of Formula I, and can be prepared according to conventional pharmaceutical techniques. In embodiments, a compound as described herein is used as the only physically active compound for the treatment of cancer, and is administered to a patient without a second active agent (such as a second anti-cancer agent).

In other embodiments, the compounds as described herein can be administered to a patient concurrently with and/or in combination with a second active ingredient. For example, referring to FIGS. 15-18, the SST7 compound and a PI3K/mTOR dual inhibitor PF05212384 act in a cooperative manner to induce apoptosis in prostate cancer PC-3 cells prostate cancer DU145 cells, colorectal cancer HCT116 cells, and liver cancer HEP3B cells, indicating one example of a combination composition for the treatment of cancer.

According to the invention, the composition can comprise a pharmaceutically acceptable carrier, which can comprise any and all solvents, dispersion media, coatings, antibacterial and antifungal agents, isotonic and absorption delaying agents, and the like, compatible with pharmaceutical administration. The use of such media and agents for pharmaceutically active substances is well known in the art. Non-limiting examples of pharmaceutically acceptable carriers comprise solid or liquid fillers, diluents, and encapsulating substances, including but not limited to lactose, dextrose, sucrose, sorbitol, mannitol, xylitol, erythritol, maltitol, starches, gum acacia, alginate, gelatin, calcium phosphate, calcium silicate, cellulose, methyl cellulose, microcrystalline cellulose, polyvinylpyrrolidone, water, methyl benzoate, propyl benzoate, talc, magnesium stearate, and mineral oil. The amount of the carrier employed in conjunction with the combination is sufficient to provide a practical quantity of material per unit dose of the compound.

The use of such media and agents for pharmaceutically active substances is well known in the art. Any conventional media or agent that is compatible with the active compound can be used. Supplementary active compounds can also be incorporated into the compositions.

Pharmaceutically acceptable carriers for oral administration comprise sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Pharmaceutically acceptable carriers for parenteral administration comprise isotonic saline, propylene glycol, ethyl oleate, pyrrolidone, aqueous ethanol, sesame oil, corn oil, and combinations thereof.

Various oral dosages forms can be employed, non-limiting examples of which comprise solid forms such as tablets, capsules, granules, suppositories and/or powders. Tablets can be compressed, tablet triturates, enteric-coated, sugar-coated, film-coated or multiple compressed, containing suitable binders, lubricants, diluents, disintegrating agents, coloring agents, flavoring agents, flow-inducing agents, and melting agents. Liquid oral dosage forms comprise aqueous solutions, emulsions, suspensions, syrups, aerosols and/or reconstituted solutions and/or suspensions. The composition may alternatively be formulated for external topical application, or in the form of a sterile injectable solution.

Pharmaceutically effective combinations can be provided as a composition comprising between 0.1 and 2000 mg/kg of a compound as described herein, such as a compound of Formula I. For example, pharmaceutically effective combinations can be provided as a composition comprising about 0.1 mg/kg, 1 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg, 1000 mg/kg, 1100 mg/kg, 1200 mg/kg, 1300 mg/kg, 1400 mg/kg, 1500 mg/kg, 1600 mg/kg, 1700 mg/kg, 1800 mg/kg, 1900 mg/kg, 2000 mg/kg of a compound as described herein.

Pharmaceutically effective combinations, such as a pill or tablet, can be comprise between 0.1 and 2000 mg of a compound as described herein, such as a compound of Formula I. For example, pharmaceutically effective combinations can comprise about 0.1 mg, 1 mg, 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, 500 mg, 525 mg, 550 mg, 575 mg, 600 mg, 625 mg, 650 mg, 675 mg, 700 mg, 725 mg, 750 mg, 775 mg, 800 mg, 825 mg, 850 mg, 875 mg, 900 mg, 925 mg, 950 mg, 975 mg, 1000 mg, 1100 mg, 1200 mg, 1300 mg, 1400 mg, 1500 mg, 1600 mg, 1700 mg, 1800 mg, 1900 mg, 2000 mg of a compound as described herein.

The present invention also comprises the formation of pharmaceutically acceptable, stable salts of the compounds as described herein with metals or amines. Non-limiting examples of metals used as cations comprise alkali metals such as Na+ or K+ and alkaline-earth metals such as $Mg^{2+}$ and $Ca^{2+}$. Non-limiting examples of amines comprise N,N-dibenzylethylenediamine, chloro-procaine, choline, diethanolamine, ethylenediamine, N-methylglucamine and procaine.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, nasal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

As an exemplary embodiment, pharmaceutical combinations of the invention can be administered orally, either in the form of tablets containing excipients such as starch or lactose, or in capsules, either alone or mixed with excipients, or in the form of syrups or suspensions containing coloring or flavoring agents. They can also be injected parenterally, for example intramuscularly, intravenously or subcutaneously. In parenteral administration, they can be used in the form of a sterile aqueous solution which can contain other solutes, such as, for example, any salt or glucose in order to make the solution isotonic.

In an embodiment, a compound of the present invention can be administered to a patient for the treatment of cancer. For oral therapeutic administration, said compounds can be mixed with excipients and used in the form of lozenges, tablets, capsules, elixirs, suspensions, syrups, wafers, chewing gum, and the like. These preparations could contain at least 0.5% of active compound, at most 0.5% of active compound, or about 0.5% active compound, but can vary depending on each form. For example, the preparations can contain between 1% and 75% approximately of the weight of each unit. The amount of active compound in such compositions should be that which is necessary for obtaining the corresponding dosage. For example, the compositions and preparations as described herein can be prepared in such a way that each oral dosage unit can contain between 0.1 mg and 300 mg of the active compound.

In parenteral therapeutic administration, the active compounds of this invention can be incorporated in a solution or suspension. Such preparations, for example, can contain at least 0.1% of the active compound, but can vary between 0.5% and 50% approximately of the weight of the preparation. For example, such preparations comprise about 0.1%, 0.5%, 1%, 5%, 10%, 15%, 25%, 30%, 35%, 40%, 45%, 50%, of the weight of the preparation. The amount of active compound in such compositions should be that which is necessary for obtaining the corresponding dosage. The compositions and preparations as described herein can be prepared in such a way that each parenteral dosage unit can contain between 0.01 mg and 1000 mg, for example between about 0.5 mg and 100 mg of the active compound, for example. While intramuscular administration can be given in a single dose or divided into up to multiple doses, such as three doses, intravenous administration can include a drip device for giving the dose by venoclysis. Parenteral administration can be performed by means of ampoules, disposable syringes or multiple-dose vials made of glass or plastic.

Pharmaceutical compositions suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). In embodiments, the composition can be sterile and should be fluid to the extent that easy syringability exists. It can be stable under the conditions of manufacture and storage and can be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyethylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, and thimerosal. In many cases, it can be useful to include isotonic agents, for example, sugars, polyalcohols such as mannitol, sorbitol, sodium chloride in the composition. Prolonged absorption of the injectable compositions can occur by including an agent in the composition which delays absorption, for example, aluminum monostearate and gelatin.

Sterile injectable solutions can be prepared by incorporating the compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds of the present invention can be administered to a subject in a single dose for the treatment of cancer, or as multiple doses over a period of time. Further, the compound can be administered at intervals of about 4 hours, 8 hours, 12 hours, 24 hours, or longer. In embodiments, the compounds of the invention can be administered continuously over a period of time, such as for 4 hours, 8 hours, 12 hours, 24 hours, or longer.

Of necessity, there will be variations which will depend on the weight and conditions of the subject to be treated and on the particular administration route selected.

Methods of Treatment

Hedgehog signaling regulates embryonic development, ensuring that tissues reach their correct size and location, maintaining tissue polarity and cellular content. In the skin, the Hedgehog pathway is critical for regulating hair follicle and sebaceous gland development. Hedgehog signaling has been implicated in regulating adult stem cells involved in maintenance and regeneration of adult tissues.

Abnormal hedgehog pathway signaling, for example inappropriate reactivation of the Hedgehog pathway, plays an important role in the pathogenesis of certain types of cancer. Loss-of-function mutations in patched and activating mutations in Smoothened have been identified in patients. Abnormal activation of the hedgehog pathway leads to development of disease through transformation of adult stem cells into cancer stem cells that give rise to the tumor. Without wishing to be bound by theory, specific inhibitors of hedgehog signaling can provide an efficient therapy for a wide range of malignancies.

Aspects of the invention are directed towards methods for treating and/or preventing in a patient a disease where the hedgehog pathway is activated. In embodiments, the disease is a cell proliferative disorder, such as cancer.

"Cancer" can refer to a general term for diseases caused by any type of tumor, such as a malignant tumor. Malignant, as applies to tumors, refers to tumors resulting from abnormal uncontrolled growth of cells and includes, but is not limited to, colorectal cancer, colon cancer, pancreatic cancer, or lung cancer.

Thus, compounds of the invention can be considered "anti-cancer agents" (also referred to as anti-neoplastic agents or anti-tumor agents), which can refer to any agent used in the treatment of cancer or neoplasm. Anti-cancer agents, when used alone or in combination with other compounds, can alleviate, reduce, ameliorate, prevent, or place or maintain in a state of remission of clinical symptoms or diagnostic markers associated with neoplasm, tumor or cancer, and can be used in methods, combinations and compositions provided herein. Non-limiting examples of such cancer comprises glioma, glioblastoma, liver cancer, colorectal cancer, stomach cancer, brain cancer, prostate cancer, breast cancer, ovarian cancer, testicular cancer, gallbladder cancer, mesothelioma, kidney cancer, sarcoma, melanoma, retinoblastoma, skin cancer, head and neck cancer, thyroid cancer, vaginal cancer, leukemia, lymphoma, lung cancer, and pancreatic cancer.

"Treatment" can refer to an approach for obtaining beneficial or desired clinical results. For example, the term "treating cancer" or "treatment of cancer" can refer to administration of a compound to a subject afflicted with a cancerous condition alleviates the cancerous condition by killing the cancerous cells, but also to an effect that results in the inhibition of growth and/or metastasis of the cancer. Non-limiting examples of cancers that can be treated by aspects of the invention comprise glioma, glioblastoma, liver cancer, colorectal cancer, lung cancer, and pancreatic cancer, and the like.

Aspects of the invention are directed towards a method of reducing cell viability by contacting a cell, such as a cancer cell, with an effective amount of a compound as described herein.

Aspects of the invention are further directed towards a method of inducing apoptosis of a cell, such as a cancer cell, by contacting a cell with an effective amount of a compound as described herein. For example, referring to FIGS. 12-15, the SST7 compound induces apoptosis in pancreatic cancer AsPC-1 cells, lung cancer A549 cells, liver cancer HEPG2 cells, and prostate cancer PC-3 cells.

Figure 17:
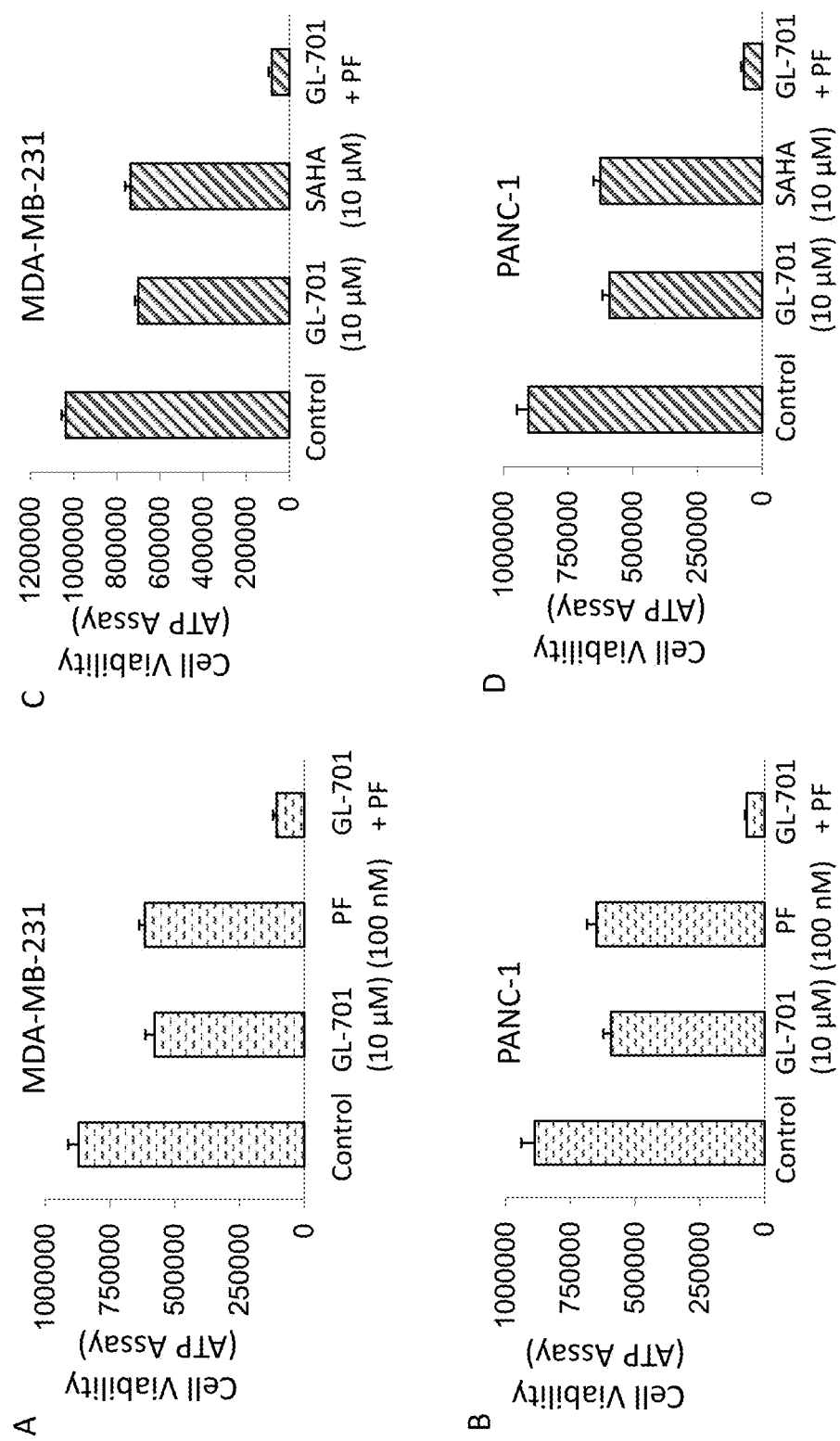
FIG. 17 shows that GL-701 co-operates with PF05212384 (PI3K/mTOR dual inhibitor) or histone deacetylase inhibitor (SAHA) in inhibiting cell viability of human breast cancer cells and pancreatic cancer cells.
Figure 18:
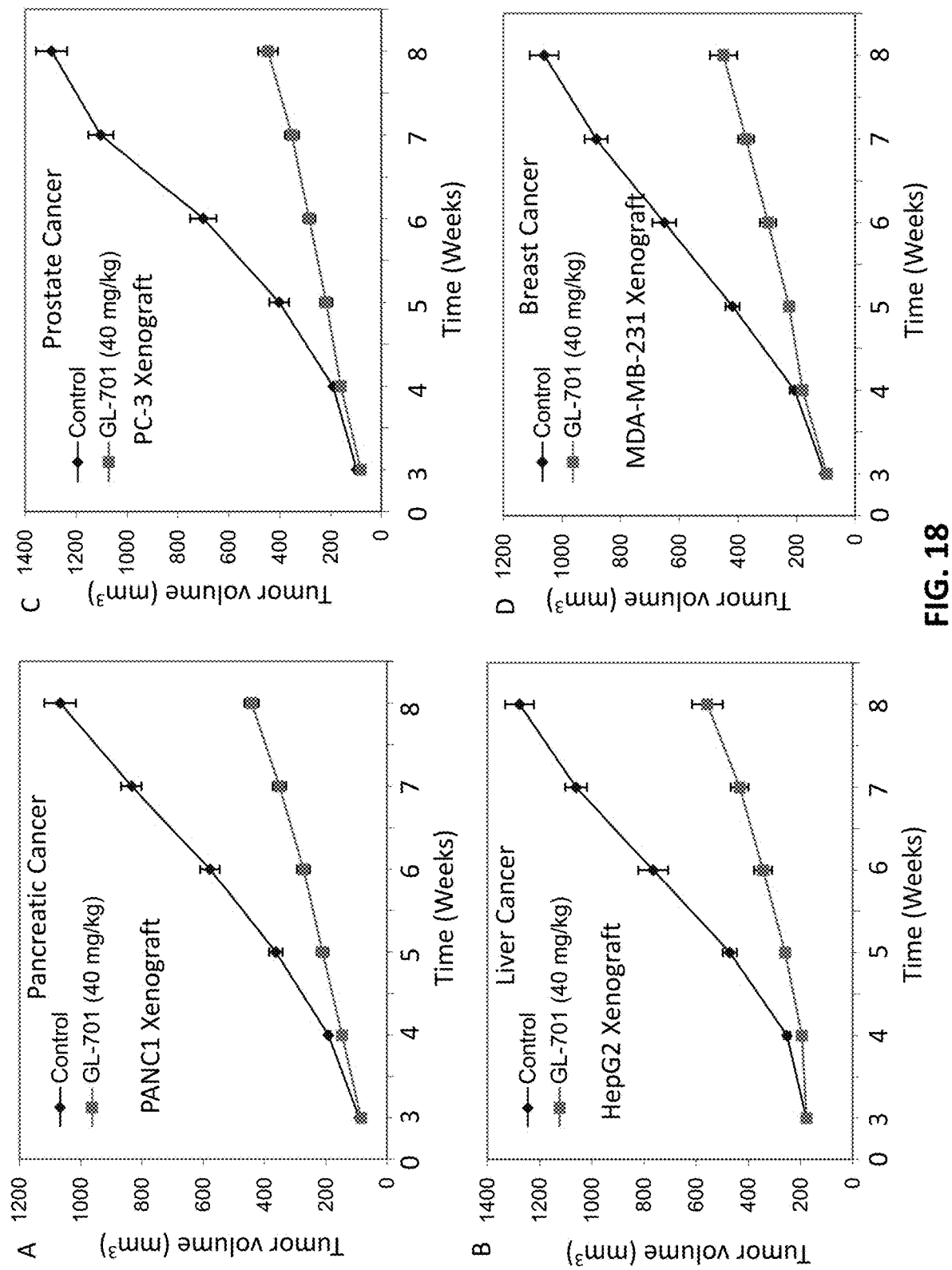
FIG. 18 shows that GL-701 inhibits xenografted tumor growth in pancreatic cancer, liver cancer, prostate cancer and breast cancer models.

Referring to FIG. 17 and FIG. 18, for example, compound SST7 and PF05212384 induce apoptosis in colorectal cancer HCT116 cells and liver cancer HEP3B cells in a synergistic fashion.

Aspects of the invention are still further directed towards a method of inhibiting cell proliferation of a cell, such as a cancer cell, by contacting a cell with an effective amount of a compound as described herein.

Aspects of the invention are also directed towards method of regulating epithelial-mesenchymal transition (EMT) by contacting a cell, such as a cancer cell, with an effective amount of a compound described herein.

Further, aspects of the invention are directed towards a method of inhibiting growth of a cancer cell or tumor by contacting a cell, such as a cancer cell, with an effective amount of a compound described herein. For example, tumor growth can be inhibited by inducing cellular apoptosis and/or inhibiting cellular proliferation.

In embodiments, the compound is a compound of Formula (I). In embodiments, the compound functions synergistically with a second active agent.

As an exemplary embodiment, compositions and methods described herein can be used to treat and/or prevent glioma in a patient. Glioma is a tumor of the brain that originates in glial cells. Glioma comprises about 30 percent of all brain tumors and about 80 percent of all malignant brain tumors. Glioma is one of the most lethal adult brain tumors. While normally functioning during embryonic development, the Hedgehog pathway has been implicated in the formation and maintenance of glioma.

In embodiments, the method comprises administering to a patient a compound described herein prior to the compound contacting a cell. Compounds of as described herein can be incorporated into pharmaceutical compositions suitable for administration to a subject in need thereof. Such compositions can comprise a compound as described herein and a pharmaceutically acceptable carrier. Thus, in some embodiments, the compounds of the invention are present in a pharmaceutical composition.

For example, a method herein can comprise administering to a patient a pharmaceutical composition comprising a therapeutically effective amount of a compound as described herein in admixture with a pharmaceutical acceptable carrier or excipient. For example, a therapeutically effective amount of the compound can be administered to a subject in need thereof so as to reduce the size of a tumor, or to prevent the tumor from growing.

Embodiments can comprise administering to a patient an effective amount of a composition as described hereinfor the treatment of a disease associated with the Hedgehog pathway, such as a cancer.

An "effective amount", "sufficient amount" or "therapeutically effective amount" can refer to an amount sufficient to effect beneficial or desired clinical result, such as killing the cancerous cells, inhibiting the growth of the cancer, and/or inhibiting the metastasis of the cancer.

Specific compositions as described herein can be administered to a subject by any suitable means, such as oral, intravenous, parenteral, subcutaneous, intrapulmonary, topical, intravitreal, dermal, transmucosal, rectal, and intranasal administration. Parenteral infusions include intramuscular, intravenous, intraarterial, or intraperitoneal administration. The compounds can also be administered transdermally, for example in the form of a slow-release subcutaneous implant or as a transdermal patch. They can also be administered by inhalation. Although direct oral administration may cause some loss of desired activity, the compounds can be packaged in such a way to protect the active ingredient(s) from digestion by use of enteric coatings, capsules or other methods known in the art.

Controlled-release pharmaceutical products have a common goal of improving drug therapy over that achieved by their non-controlled counterparts. The use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Solutions or suspensions used for parenteral, intradermal, or subcutaneous application can include, for example, the following components: a sterile diluent such as water for injection, saline solution, fixed oils, polyethylene glycols, glycerine, propylene glycol or other synthetic solvents; anti-inflammatory agents; antioxidants such as ascorbic acid or sodium bisulfite; chelating agents such as ethylenediamine tetraacetic acid; buffers such as acetates, citrates or phosphates and agents for the adjustment of tonicity such as sodium chloride or dextrose. pH can be adjusted with acids or bases, such as hydrochloric acid or sodium hydroxide.

The dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

In some embodiments, the therapeutically effective amount is at least about 0.1 mg/kg body weight, at least about 0.25 mg/kg body weight, at least about 0.5 mg/kg body weight, at least about 0.75 mg/kg body weight, at least about 1 mg/kg body weight, at least about 2 mg/kg body weight, at least about 3 mg/kg body weight, at least about 4 mg/kg body weight, at least about 5 mg/kg body weight, at least about 6 mg/kg body weight, at least about 7 mg/kg body weight, at least about 8 mg/kg body weight, at least about 9 mg/kg body weight, at least about 10 mg/kg body weight, at least about 15 mg/kg body weight, at least about 20 mg/kg body weight, at least about 25 mg/kg body weight, at least about 30 mg/kg body weight, at least about 40 mg/kg body weight, at least about 50 mg/kg body weight, at least about 75 mg/kg body weight, at least about 100 mg/kg body weight, at least about 200 mg/kg body weight, at least about 250 mg/kg body weight, at least about 300 mg/kg body weight, at least about 3500 mg/kg body weight, at least about 400 mg/kg body weight, at least about 450 mg/kg body weight, at least about 500 mg/kg body weight, at least about 550 mg/kg body weight, at least about 600 mg/kg body weight, at least about 650 mg/kg body weight, at least about 700 mg/kg body weight, at least about 750 mg/kg body weight, at least about 800 mg/kg body weight, at least about 900 mg/kg body weight, or at least about 1000 mg/kg body weight.

A therapeutically effective dose can depend upon a number of factors known to those of ordinary skill in the art. The dose(s) can vary, for example, depending upon the identity, size, and condition of the subject or sample being treated, further depending upon the route by which the composition is to be administered, if applicable, and the effect which the practitioner desires. These amounts can be readily determined by the skilled artisan.

A compound as described herein or composition comprising the same can be administered to the subject one time (e.g., as a single injection or deposition). Alternatively, administration can be once or twice daily to a subject in need thereof for a period of from about 2 to about 28 days, or from about 7 to about 10 days, or from about 7 to about 15 days. It can also be administered once or twice daily to a subject for a period of 1, 2, 3, 4, 5, 6, 7, 8, 9, 10, 11, 12 times per year, or a combination thereof.

Single unit dosage forms of the disclosure are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal (e.g., cream, lotion, or dermal spray) or transcutaneous administration to a subject. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions or solutions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms for parenteral administration to a subject.

The composition, shape, and type of dosage forms of the disclosure will typically vary depending on their use. Further, the dosage can vary depending upon known factors such as the pharmacodynamic characteristics of the active ingredient and its mode and route of administration; time of administration of active ingredient; age, sex, health and weight of the recipient; nature and extent of symptoms; kind of concurrent treatment, frequency of treatment and the effect desired; and rate of excretion.

For example, a dosage form used in the acute treatment of a disease can contain larger amounts of one or more of the active agents it comprises than a dosage form used in the chronic treatment of the same disease. Similarly, a parenteral dosage form can contain smaller amounts of one or more of the active agents it comprises than an oral dosage form used to treat the same disease. These and other ways in which specific dosage forms encompassed by this disclosure will vary from one another will be readily apparent to those skilled in the art. See, e.g., Remington's Pharmaceutical Sciences, 18th ed., Mack Publishing, Easton Pa. (1990).

Any of the therapeutic applications described herein can be applied to any subject (also referred to as a "patient") in need of such therapy, including, for example, a mammal such as a mouse, a rat, a dog, a cat, a cow, a horse, a rabbit, a monkey, a pig, a sheep, a goat, or a human. In some embodiments, the subject is a mouse, rat, pig, or human. In some embodiments, the subject is a mouse. In some embodiments, the subject is a rat. In some embodiments, the subject is a pig. In some embodiments, the patient is a human.

Medical Kits

Aspects of the invention are directed towards a medical kit suitable for the treatment of cancer or an inflammatory condition comprising printed instructions for administering a compound as described herein to a subject in need thereof; and/or a pharmaceutical composition comprising a compound as described herein and a pharmaceutically acceptable carrier. A "kit" or "medical kit" of the disclosure comprises a dosage form of a compound of the disclosure or a pharmaceutically acceptable salt, solvate, hydrate, stereoisomer, prodrug, or clathrate thereof. A kit can also include two or more compounds as described herein, either in combination, such as in a single tablet, or provided separately, such as in two or more tablets.

Kits can further comprise additional active agents, examples of which are described herein. Kits of the disclosure can further comprise devices that are used to administer the active ingredients. Examples of such devices include, but are not limited to, syringes, drip bags, patches, and inhalers. Kits can also comprise printed instructions for administering the compound to a subject.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Design, Synthesis, and Evaluation of a Novel Inhibitor Against Therapeutic Targets in Glioblastoma Glioma is known as a tumor of the brain that originates from the glial cells. Glioblastoma multiforme (GBM) is classified as Grade IV type of glioma as per the classification of the World Health Organization (WHO) and is one of the most lethal brain tumor that comprises about 80 percent of all malignant brain tumors [1].

The Hedgehog (Hh) signaling pathway is closely associated with embryonic development, including the formation and maintenance of glioma [2, 3]. Gliomas are important biological factors responsible for actions like cancer invasion, metastasis, drug resistance, relapse and hence Hh signaling is believed to be an important target for cancer therapy[4]. Recently, both natural and synthesized small-molecule inhibitors of Hh signaling have been investigated as the potential cancer treatment. There are four key components involved in hedgehog signaling including Hedgehog ligand, Hedgehog ligand patched receptor, smoothened (SMO) cell surface signal transducer, and the Gli transcription factors (downstream effectors). Patched receptor normally suppresses the activity of SMO, but when hedgehog ligand binds to the patched receptor, it relieves SMO, which ultimately leads to the transcription of various Gli target genes. It is reported that around one-third of all human GBM patients exhibit hyperactive Hh signaling, often due to mutations in the Smo, Patched receptor or Gli target genes. Importantly, several antagonists targeting SMO are in advanced-stage clinical trials that inhibit tumor growth and reduce symptoms in adult patients. Thus SMO has emerged as an attractive therapeutic target for small-molecule inhibitor as antitumor drug development. Recently, molecular docking studies have been exploited to identify the direct binding of inhibitors to the transmembrane helices of SMO [5].

Design Consideration

β-Amino alcohol is an important pharmacophore in the vast range of synthetic as well as biologically active anti-cancer compounds[6]. β-Amino alcohol can either be acy-lated, alkylated, connected as a linker or contained within rings in these molecule, e.g., bestatin, daunorubicin, elsami-cin A, and doxorubicin.

Similarly, literature also revealed that heterocyclic ben-zoxazole and benzimidazole ring are isosteres of naturally occurring guanine and adenine nucleotides [7] and possess anticancer activities [7, 8]. Apart from them, several other heterocyclic compounds are reported as inhibitors of hedge-hog signaling pathway in nanomolar concentrations that inhibit oncogenic Smo [9].

The poor aqueous solubility and toxicity profile are the main challenges of these heterocyclic compounds; therefore there remains a need to develop new compounds with better activity and devoid of toxicity. Here we developed the Hh-targeting small molecules by linking the benzoxazole with 1,3-bis(phenylamino)propan-2-ol having active β-Amino alcohol active moieties. The resulting hybrids were synthesized and evaluated as the inhibitor of hedgehog signaling pathway (FIG. 1).

Material and Method

General Synthesis of 4-benzo[d]oxazol-2-yl) aniline (Compound 3)

2-Aminophenol 1 (0.026 mol), para amino benzoic acid 2 (3.63 g, 0.026 mol) was mixed with polyphosphoric acid, and heated at 180° C. with continuous stirring for 8 h then poured into ice-cold 20% aqueous sodium carbonate. The solid product was collected, washed with water and recrystallized with methanol-water mixture (50:50). Physio-chemical characterization and NMR spectra: Yield: 65%. mp 180-183° C.; $^1$H NMR (CDCl$_3$, 500 MHz): δ 8.08-8.07 (d, 2H), 7.71-7.67 (m, 1H), 7.55-7.49 (m, 1H), 7.32-7.28 (m, 2H), 6.79-6.77 (m, 2H) and 4.08 (s, 2H).

Synthesis of 1-(4-(benzo[d]oxazol-2-yl)phenylamino)-3-chloropropane-2-ol (5)

The compound 3 (0.0025 mmol) was allowed to absorb on Silica gel (60-120 mesh, 50% w/w), further, epichlorohydrin 4 (0.0025 mmol) was added at room temperature under nitrogen atmosphere. The solid reaction mixture has magnetically stirred the mixture for 72 hrs at room temperature. After completion of the reaction, the solid mixture was diluted with Et$_2$O (15 ml) followed by addition of a few drops of water (to settle down the silica). The silica was separated by decantation of the supernatant ethereal solution and then washed with Et$_2$O (10 ml). The combined ethereal solutions were dried (Na$_2$SO$_4$) and concentrated under vacuum to afford 1-(4-(benzo[d]oxazol-2-yl)phenylamino)-3-chloropropane-2-ol (5), which was carried to the next step directly without any further purification.

Synthesis of 4-(benzo[d]oxazol-2-yl)-N-(oxiran-2-ylmethyl)aniline (Compound 6)

To a solution of 5 (1.0 mmol) and KOH powder (1.2 mmol) in diethylether was stirred at room temperature for 24 hours. The mixture was diluted with EtOAc and washed with 1M HCl and brine. The organic layer was dried with anhydrous sodium sulphate and concentrated to give crude product. It was further purified by silica gel chromatography using 20% EtOAc/Hex to get product 4-(benzo[d]oxazol-2-yl)-N-(oxiran-2-ylmethyl)aniline (6). Physio-chemical characterization and NMR spectra: Yield: 40%. $^1$H NMR (500 MHz, CDCl$_3$) δ 7.61-7.47 (m, 2H), 7.37 (d, J=3.6 Hz, 2H), 7.31 (d, J=11.1 Hz, 2H), 6.80-6.66 (m, 2H), 4.43 (s, 1H), 3.26 (d, J=6.8 Hz, 2H), 3.00 (s, 1H), 2.83 (s, 1H), 2.58 (s, 1H).

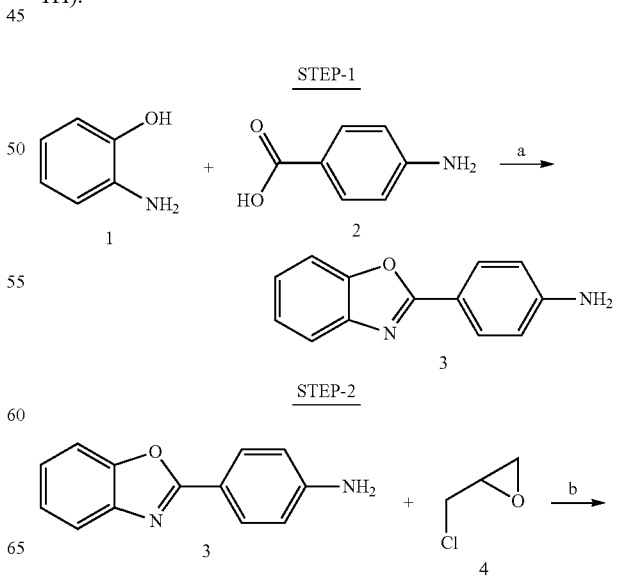

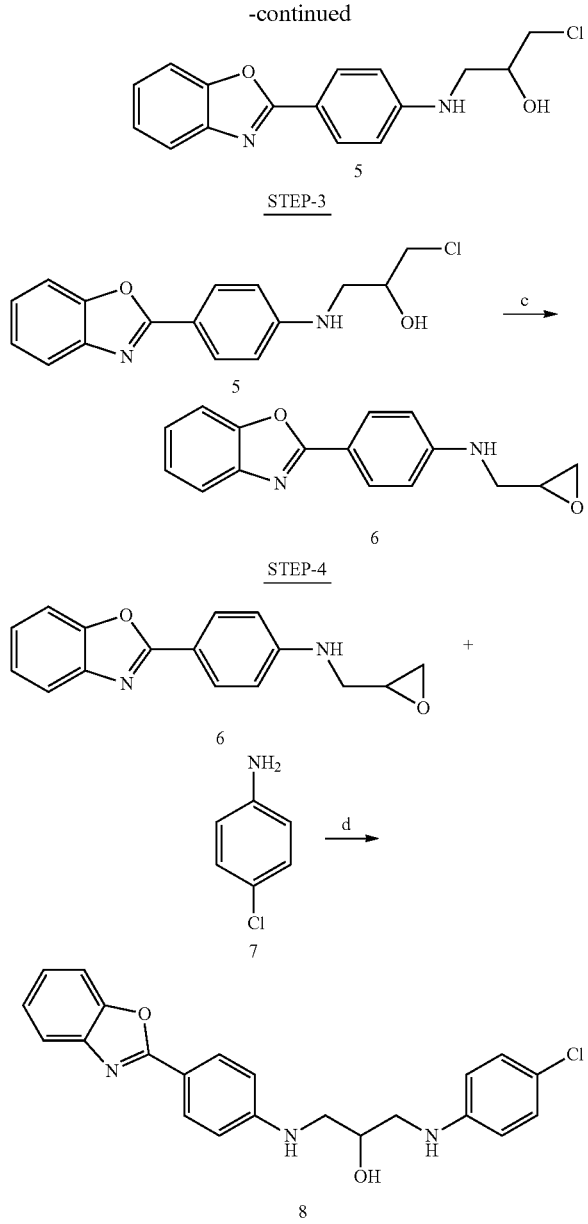

Scheme 1: Synthesis of Compound 3, 6, and 8. Reagents and conditions: (a) polyphosphoric acid, 170-180° C., 8 h; (b) Silica gel (60-120 mesh, 50% w/w), 72 h; (c) KOH, diethylether, 24 h; (d) ethanol, 60-65° C., 5 h. (see also FIG. 2)

Synthesis of 1-(4-(benzo[d]oxazol-2-yl)phenylamino)-3-(4-chlorophenylamino)propane-2-ol (Compound 8)

A mixture of 4-chloroaniline 7 (0.003 mmol) and oxirane 6 (0.001 mmol) were refluxed in ethanol for 5 h and left standing for 18 h at room temperature. The mixture was evaporated, the residue was subjected to vacuum distillation to afford 1-(4-(benzo[d]oxazol-2-yl)phenylamino)-3-(4-chlorophenylamino)propane-2-ol (8). Yield: 74%. $^1$H NMR (500 MHz, CDCl$_3$) δ 7.91-6.50 (m, 13H), 5.96 (m, 1H), 5.146 (m, 1H), 3.87-3.86 (m, 1H), 3.30-3.0 (m, 4H)

Protein Preparation & Grid Generation:

In search of new hits with a dual binding affinity with SMO receptor. The 3D structure of SMO receptor complexed with ligand LY2940680 [4-fluoro-N-methyl-N-(1-[4-(1-methyl-1H-pyrazole-5-yl)phthalazin-1-yl]piperidin-4-yl)-2-(trifluoromethyl)benzamide] was collected from protein data bank (PDB CODE: 4JKV). The retrieved structure may consist of water molecules, co-crystallized ligands, metal ions and co-factors. Protein preparation wizard was used for the crystal structure preparation of SMO. The solved structure is a dimer, and only chain A was used for the docking study. The binding site was identified by determining the position of the ligand LY-2940680. The structure was processed by deletion of water molecule beyond 5 Å, filling of missing side chain and loops, assign of bond order and the addition of hydrogen atoms into the crystal structure. Further, structure refinement and restrain minimization was done using OPLS force field. The grid was generated by using the co-crystallized ligand present as the centroid of the active site having a box volume of 10*10*10 Å. Further docking of the prepared ligand was performed using the generated grid, and lowest energy level and docked conformation was retained. The default settings were used for all other parameters. The extra precision (GLIDE-XP) protocol implemented in GLIDE was used for docking (Schrödinger 2016-1).

Molecular Dynamics Experimental:

The binding stability and pattern of the docked complex of compound 8 was analyzed on human smoothened 7TM receptor (PDB Code: 4JKV) protein. The 10 ns molecular dynamics simulation run was performed from the docked complex of compound 8 on the protein using the Desmond module of Schrödinger Maestro 10.5.014 program. The cubic simulation box was prepared to build the system. The TIP3P explicit water model was used, and the minimum distance of 10 Å was set between box wall and protein-ligand complex. The system was neutralized with the addition of counter ions, and the isosmotic salt environment was provided with 0.15M NaCl. The system was further minimized with maximum 2000 interactions with convergence criteria of 1 kcal/mol/Å. The minimized docked complex was further subjected to molecular dynamics simulations for 10 ns. The recording interval energy was kept at 1.2 ps, and the trajectory was set at 9.6. The simulation run was performed at the constant number of atoms (N), pressure (P) and temperature (T) (NPT) ensemble at the temperature of 300K and 1.013 bars atmospheric pressure. The generated trajectory was utilized to generate simulation interaction diagrams to get the results.

Results and Discussion

Chemistry:

4-(Benzo[d]oxazol-2-yl) aniline (3) was synthesized from the condensation of O-amino phenol (1) with p-amino benzoic acid (2) in the presence of polyphosphoric acid at 180° C. (Scheme 1). The aniline (3) was then reacted with epichlorohydrin (4) through nucleophilic substitution reaction using silica gel (SiO$_2$). The silica proficiently catalyzes the opening of epoxide ring as epichlorohydrin reacts with nucleophiles at the epoxide end and generates alkoxide ion. However, due to the delocalization of the negative charge on alkoxide anion in conjugation with the oxygen of silica, the closure of the epoxide not take place and resulted in open halo amino phenol (5). In the next step dehydrochlorination of halo aminophenol occurs using potassium hydroxide to generate corresponding oxirane ring (6). Further, the oxirane was condensed with the amine (7) yielded the corresponding final N-aryl derivatives of amino alcohol (8).

Figure 20:
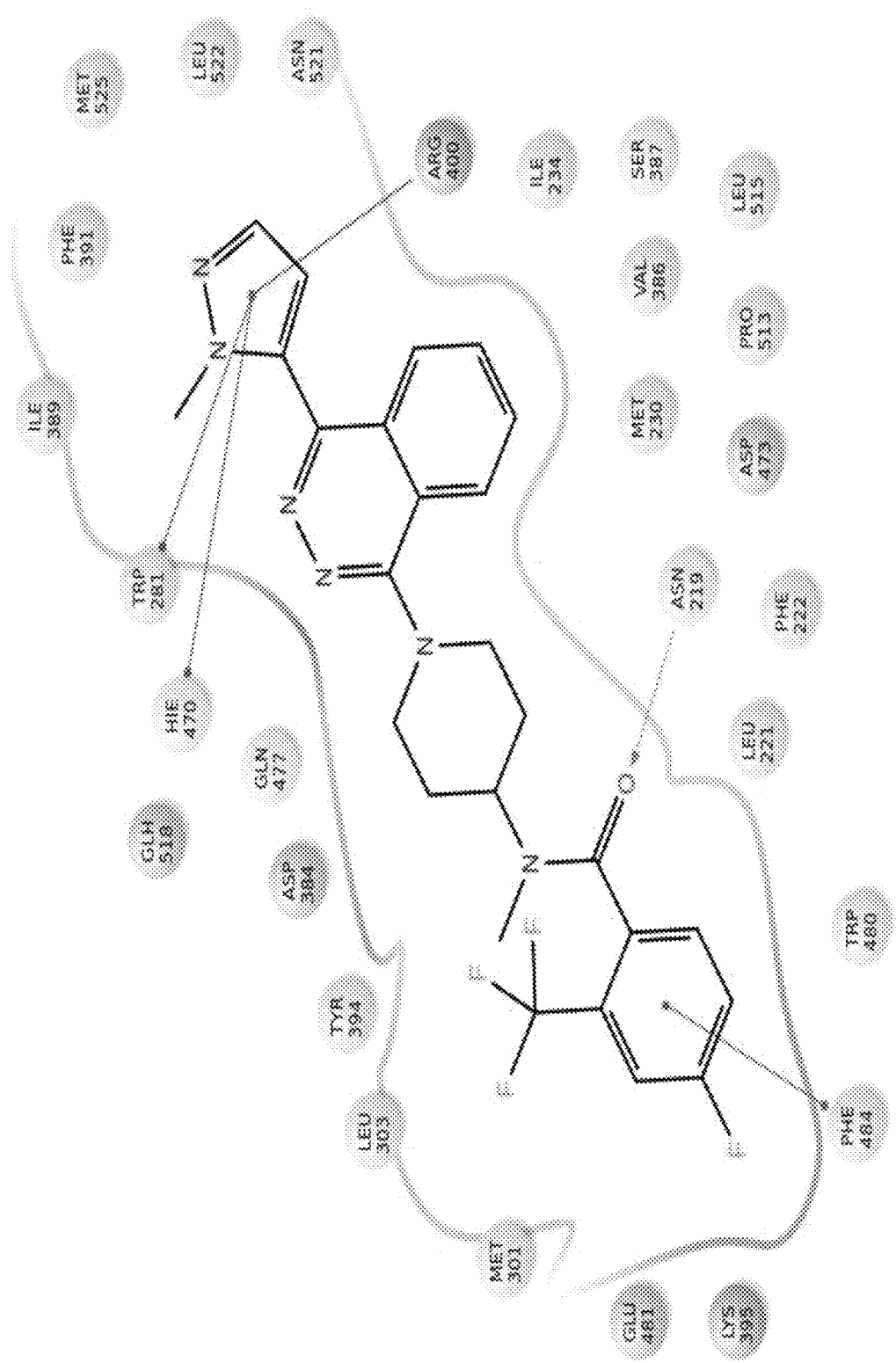
FIG. 20 shows binding pose predicted by Glide-XP of SMO receptor and standard LY2940680.

Molecular Docking and Interaction Analysis of Compound 8 and LY2940680 on SMO Receptor Active Transmembrane Binding Site:

The docking results revealed that LY2940680 has highest XP score of −11.60 Kcal/mole against SMO. On the other hand, Compound 8 shows XP score −10.66 Kcal/mole. The details of the interaction energy and interacting residues with all the identified hits are shown in FIG. 7. The SMO receptor binding pocket has a narrow and long shape and is connected to the extracellular aqueous environment through a small opening formed by an extracellular domain (ECD) composed of an extracellular cysteine-rich domain (CRD) and an ECD linker domain. This orifice probably facilitates small-molecule ligand entry into the transmembrane core region. Residues from the extracellular tips of helices I, II, V, and VII interact with phthalazine ring of LY2940680 via a hydrogen bond to Arg400 (FIG. 20). Most of the other contact residues belong to the ECD linker domain and ECLs. The ligand was mediating the 3π interaction with Trp-281, Hie-470, Phe-484, Arg-400, it also showed hydrophobic interaction with other important residues have a role in the conformational properties and dynamics of the pocket.

Figure 8:
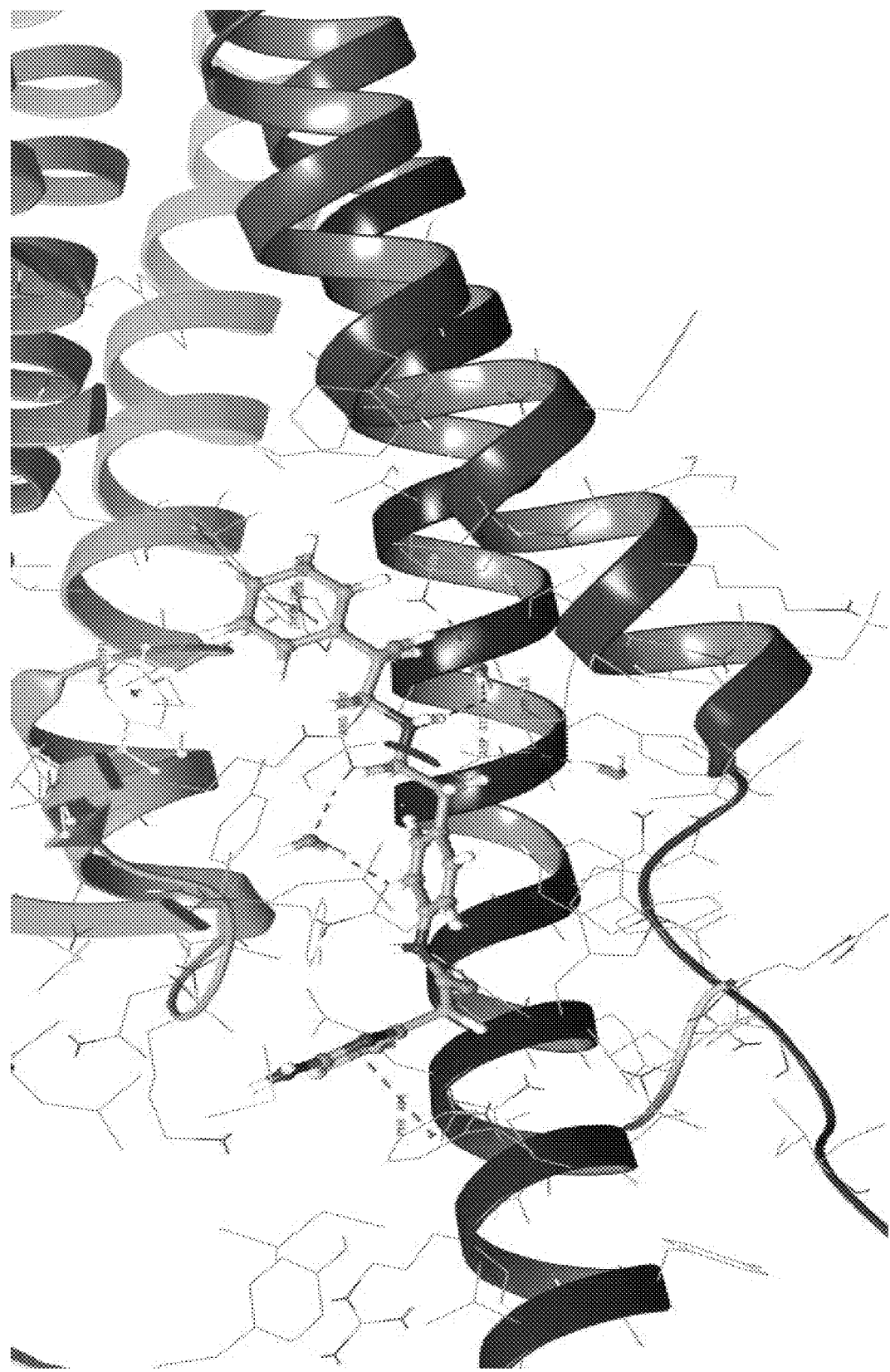
FIG. 8 shows 3-D binding pose predicted by Glide-XP of SMO receptor and Compound 8.
Figure 21:
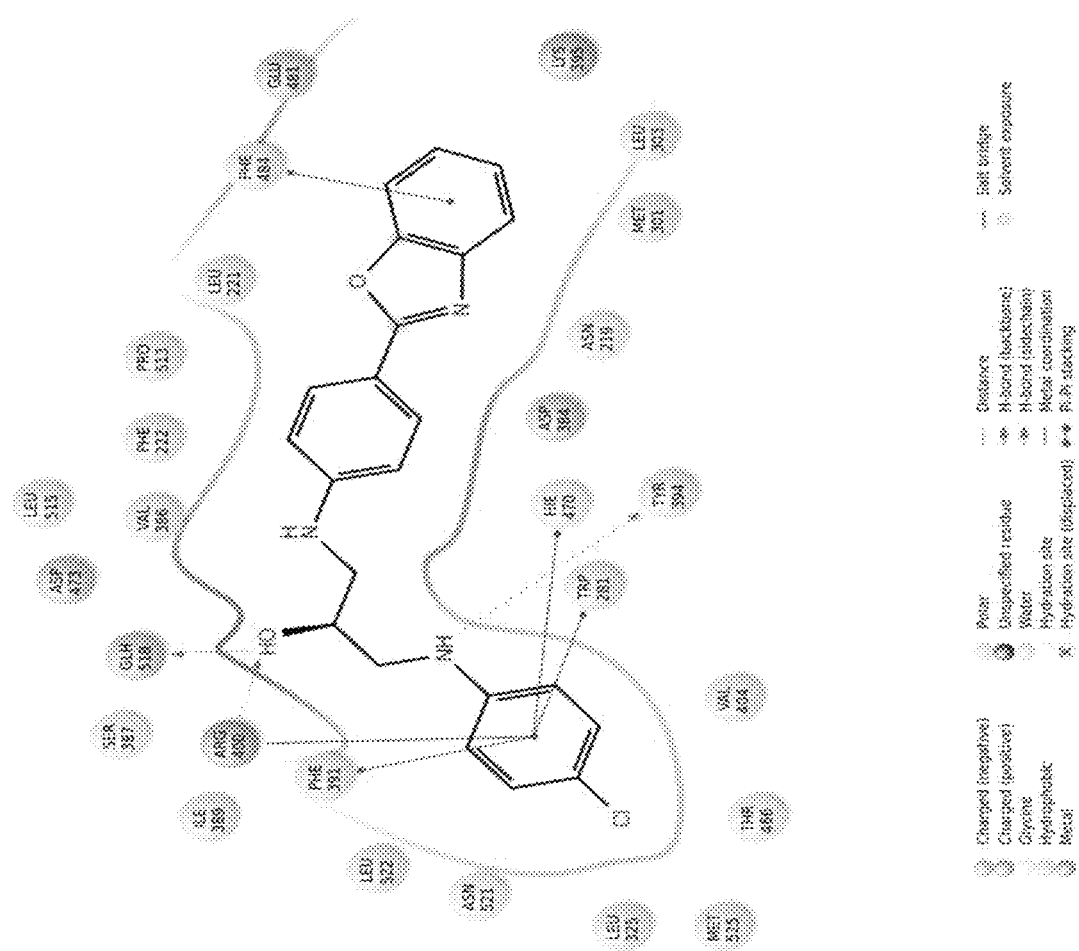
FIG. 21 shows 2D binding pose predicted by Glide-XP of SMO receptor and Compound 8.

Compound 8 showed 3 Hydrogen bonding with Glh518, Arg400, & Tyr394 and 4π interaction with Trp281, Phe391, Phe484, and His470. Compound 8 also exhibited strong hydrophobic interaction with other residues at the active site (FIG. 8 and FIG. 21).

Figure 9:
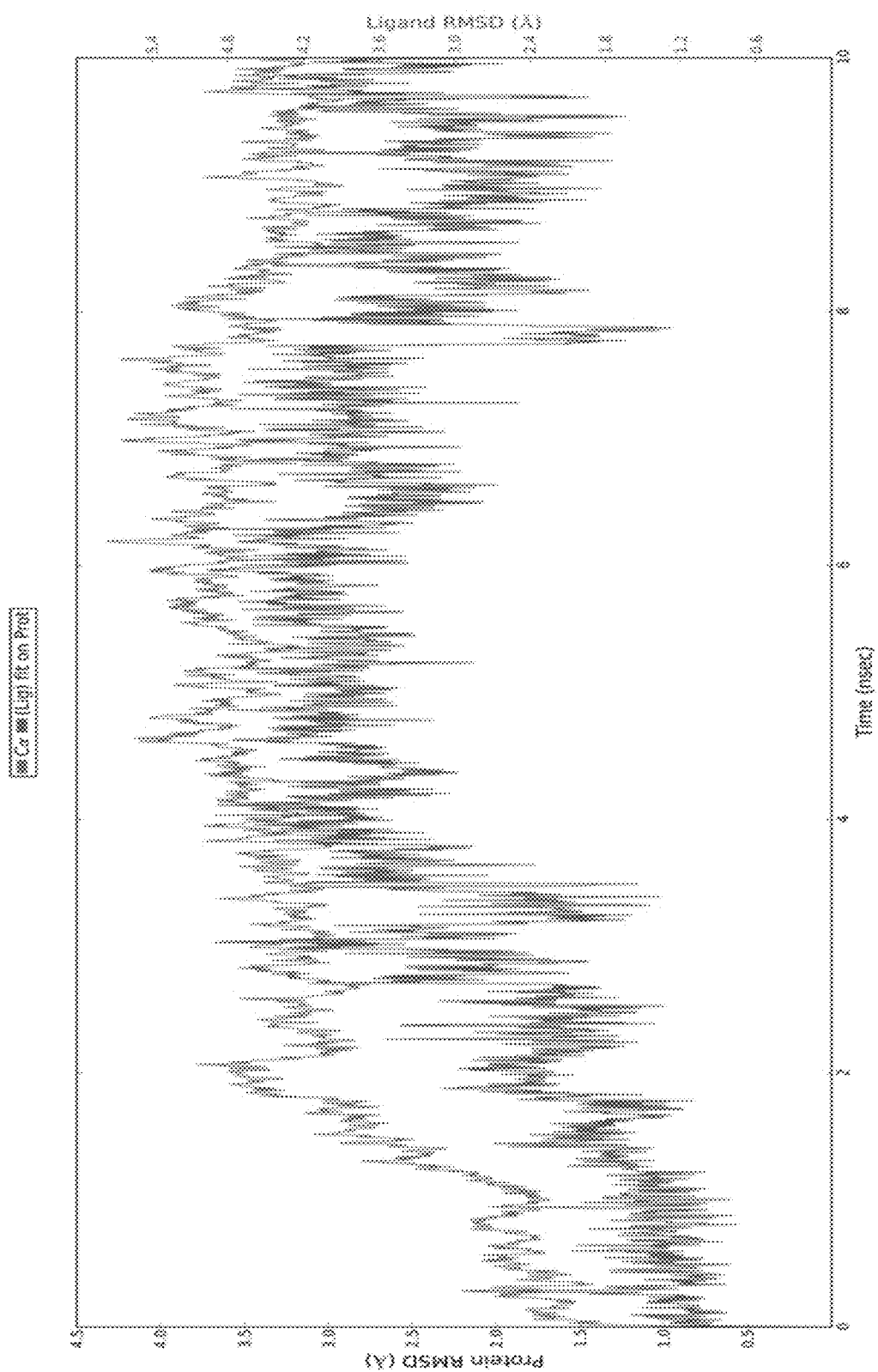
FIG. 9 shows molecular dynamics simulation study. RMSD fluctuations of protein backbone (green) and Compound 8 (Red) for 10 ns simulation run on 4JKV.

The preceding findings of molecular docking analysis made it worthwhile to confirm the binding mode stability and integrity of complex with molecular dynamics simulations run. The simulation run of 10 ns was performed for compound 8 independently on human smoothened 7TM receptor (PDB Code: 4JKV) protein. The overall stability of the system was evaluated by RMSD (root mean square deviation) and RMSF (root mean square fluctuation) calculations. RMSD calculations are based on the alignment of protein backbone with the reference initial backbone structure. The RMSD calculations provide insights of structural stability and conformations throughout the simulations run. The results of the RMSD values for compound 8 simulation runs confirmed the energetically stable trajectories and integrity throughout the simulations with average fluctuations in the range of 1-3 Å (FIG. 9). Further interactions factions and accommodation in the active binding site for all the ligand was analyzed through the simulations run.

Simulation interaction diagram module was utilized to generate stacked bar chart, which showed the normalized interaction over the course of trajectory. The stacked bar chart showed four types of ligand-protein interactions including Hydrogen Bonds, Hydrophobic, Ionic, and Water bridges. A schematic protein-ligand contacts diagram was also generated with contacts of more than 30% throughout the simulation run. Further, a timeline representation of all amino acid residues with ligand was also generated and analyzed.

Figure 10:
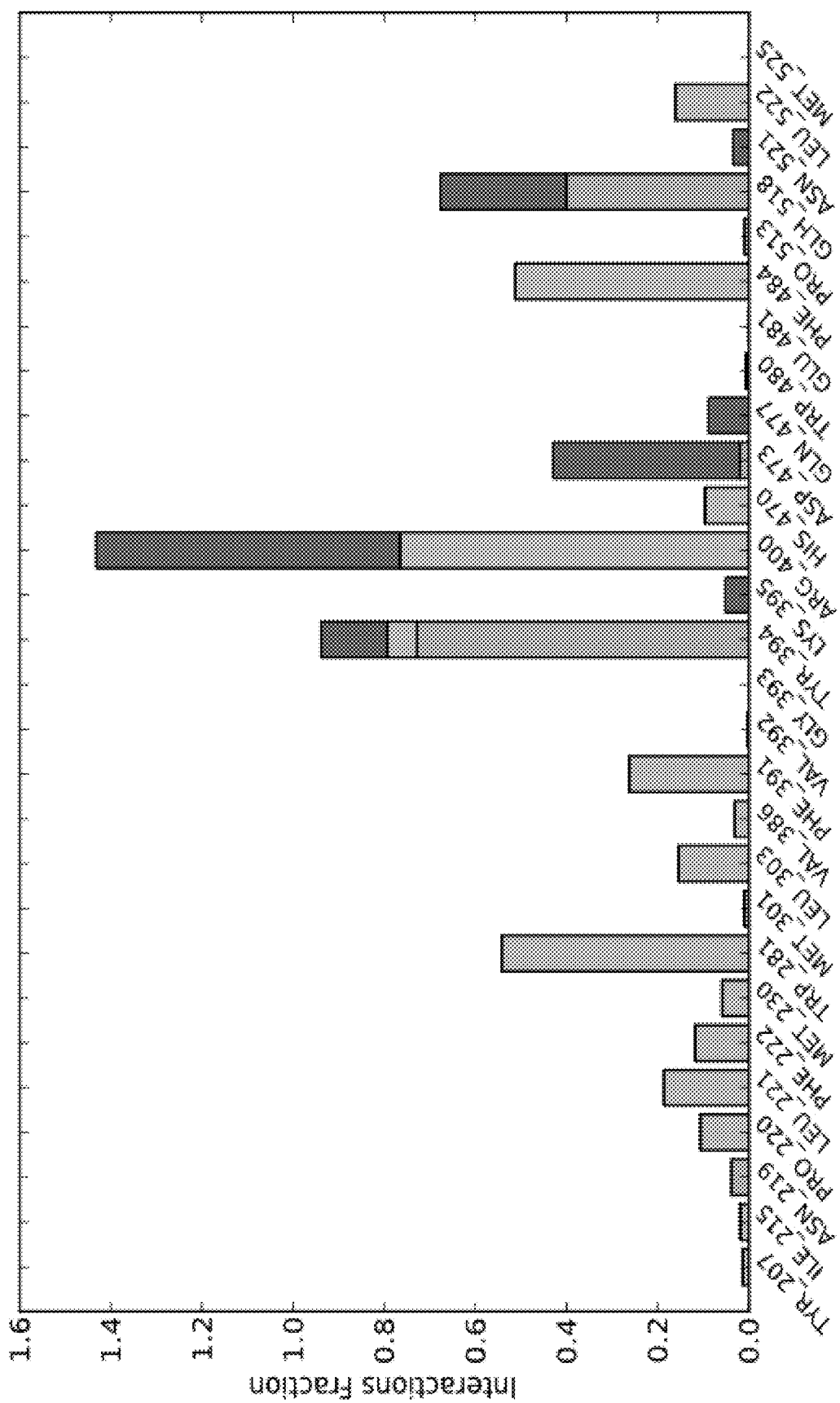
FIG. 10 shows protein-ligand contacts of Compound 8 for 10 ns simulation run on 4JKV.
Figure 11:
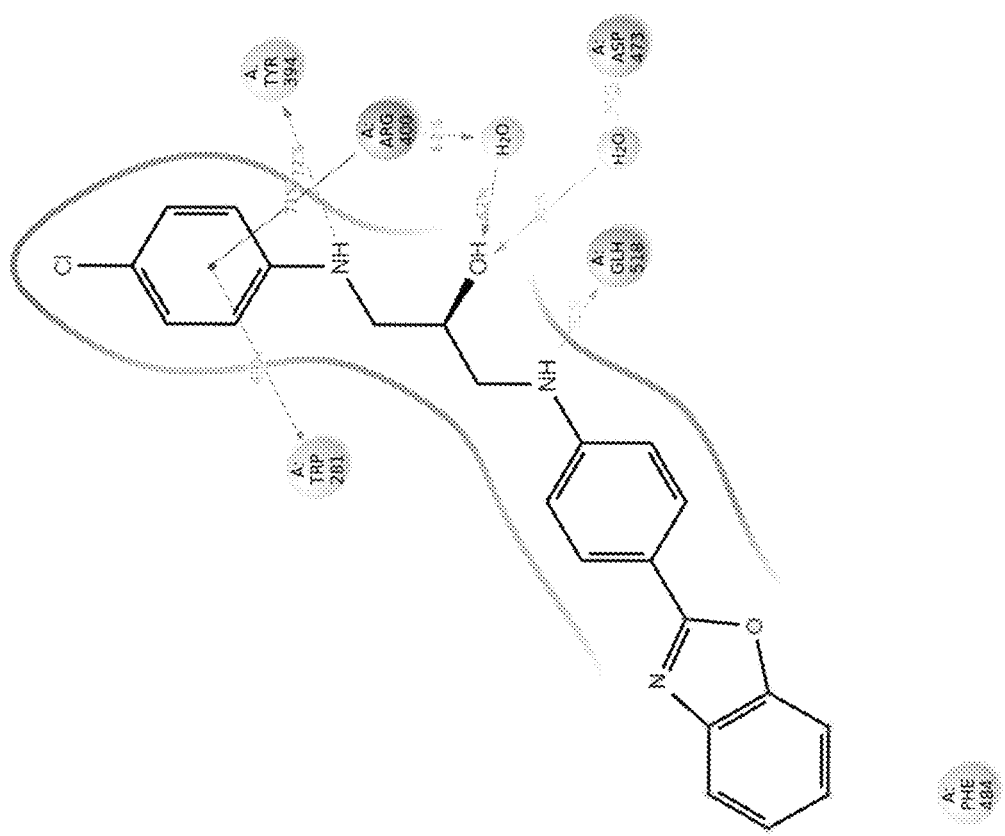
FIG. 11 shows ligand-protein contacts of Compound 8 for 10 ns simulation run on 4JKV.
Figure 12:
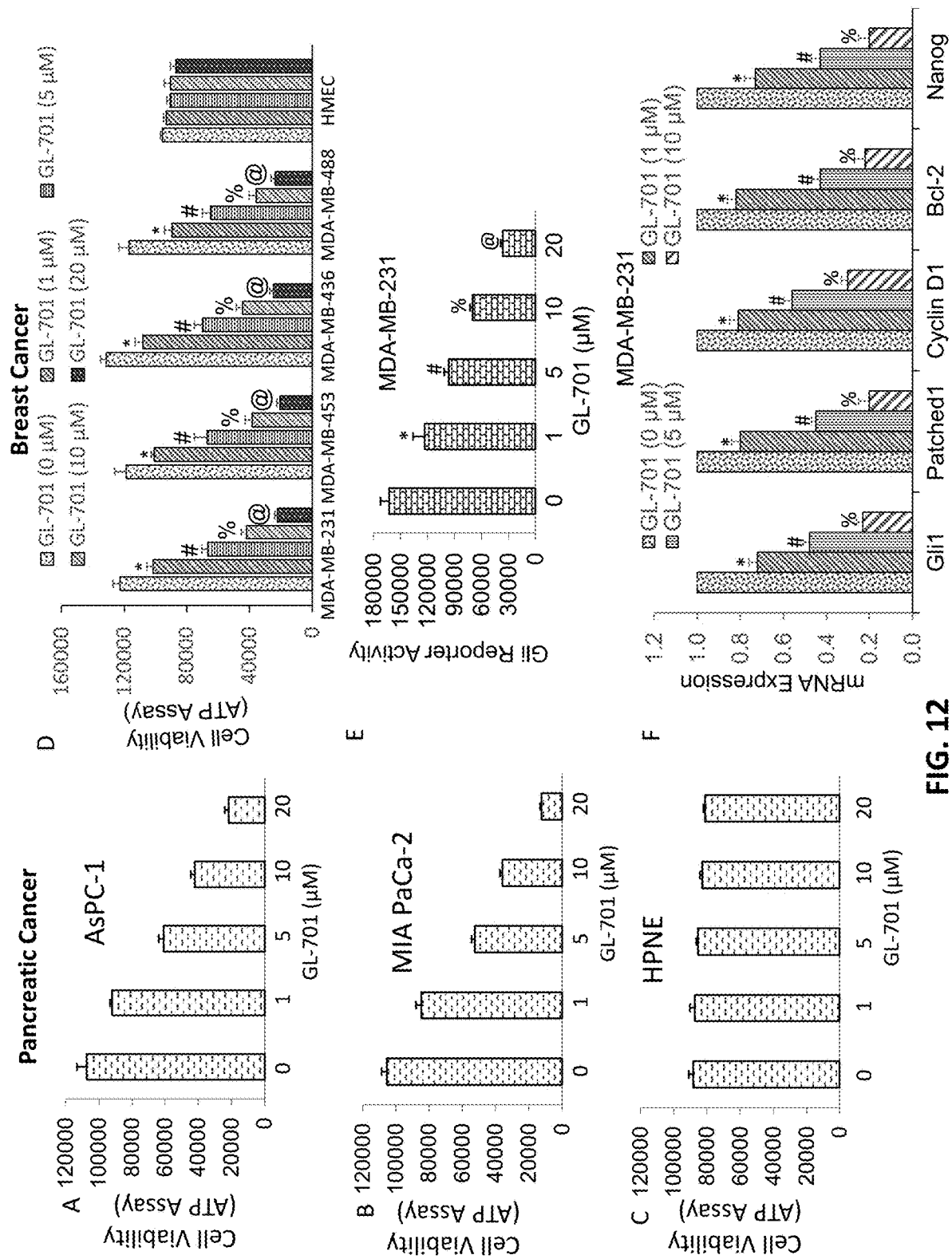
FIG. 12 shows GL-701 (also referred as SST7) inhibits cell viability of human pancreatic cancer cells (A and B), but has no effect on human normal pancreatic ductal epithelial (HPNE) cells (C). GL-701 inhibits cell viability of human breast cancer cells but has no effect on human normal ductal epithelial (HMEC) cells (D). GL-701 inhibits Gli reporter activity (E), and expression of Gli1, Patched-1, Cyclin D1, Bcl-2, and Nanog in breast cancer cells (F).
Figure 13:
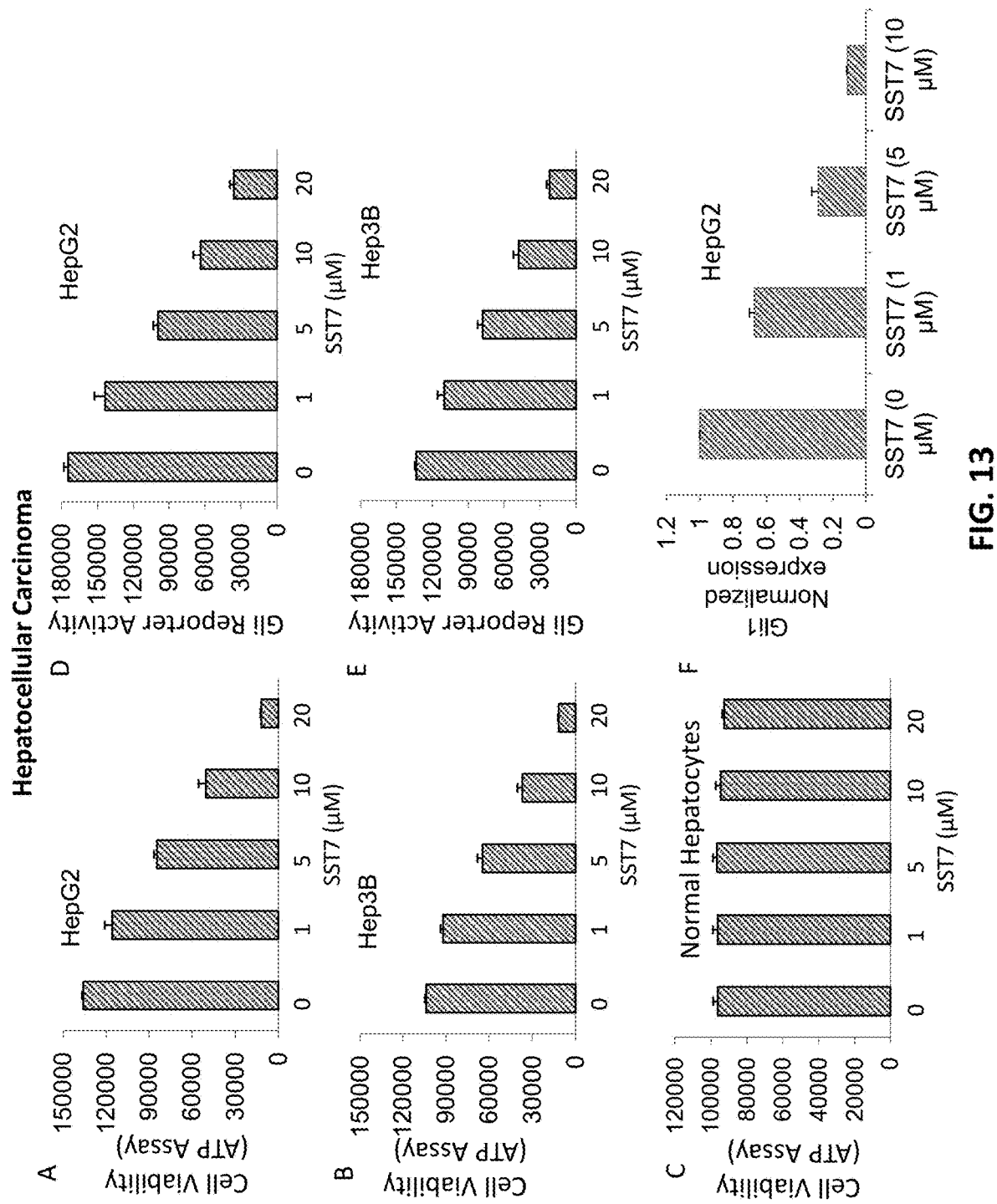
FIG. 13 shows GL-701 inhibits cell viability in hepatocarcinoma (HCC)/liver cancer cells, but has no effect on human normal hepatocytes. GL-701 inhibits Gli pathway in HCC.
Figure 14:
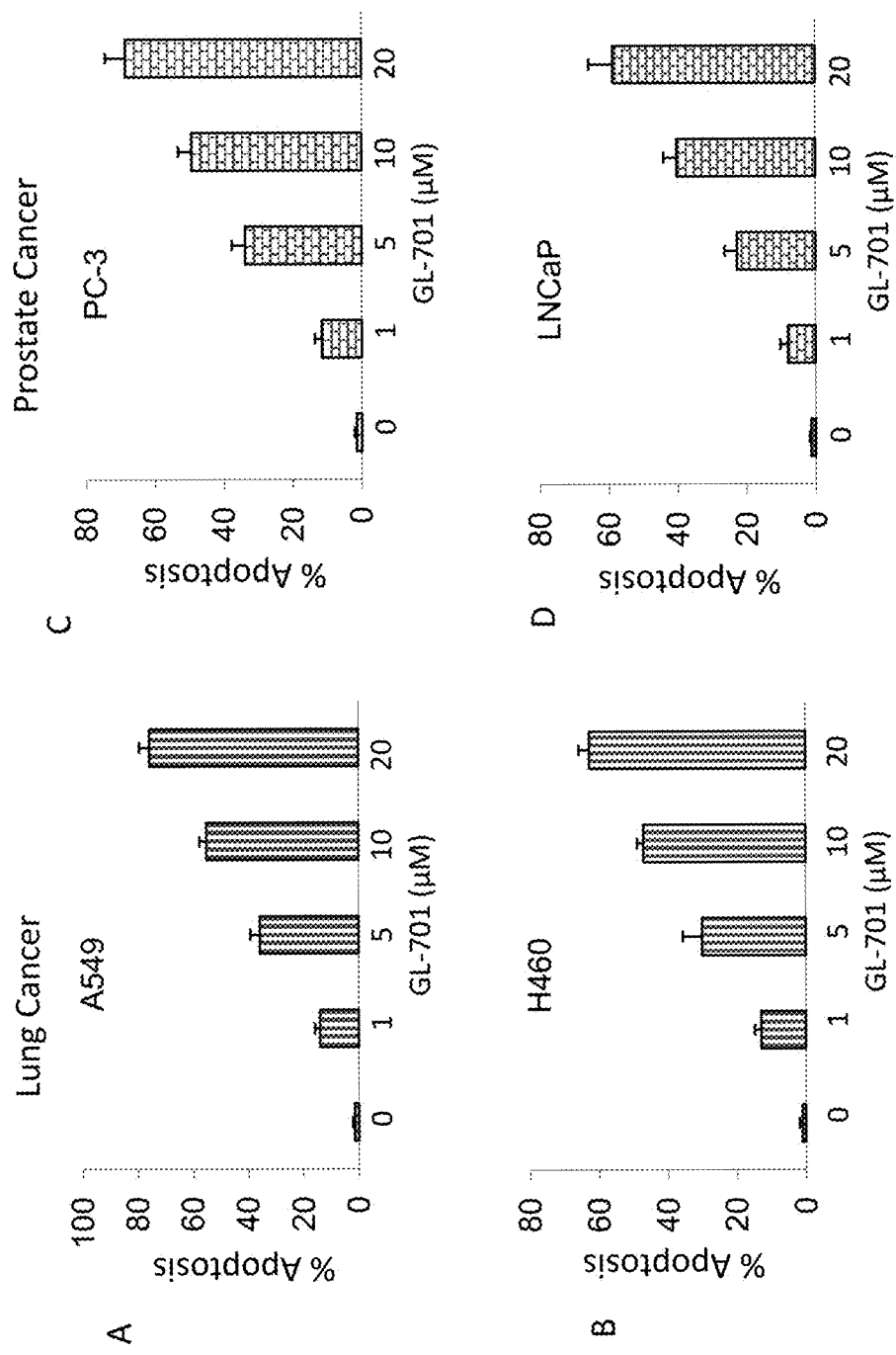
FIG. 14 shows GL-701 induces apoptosis in lung cancer and prostate cancer cells.
Figure 15:
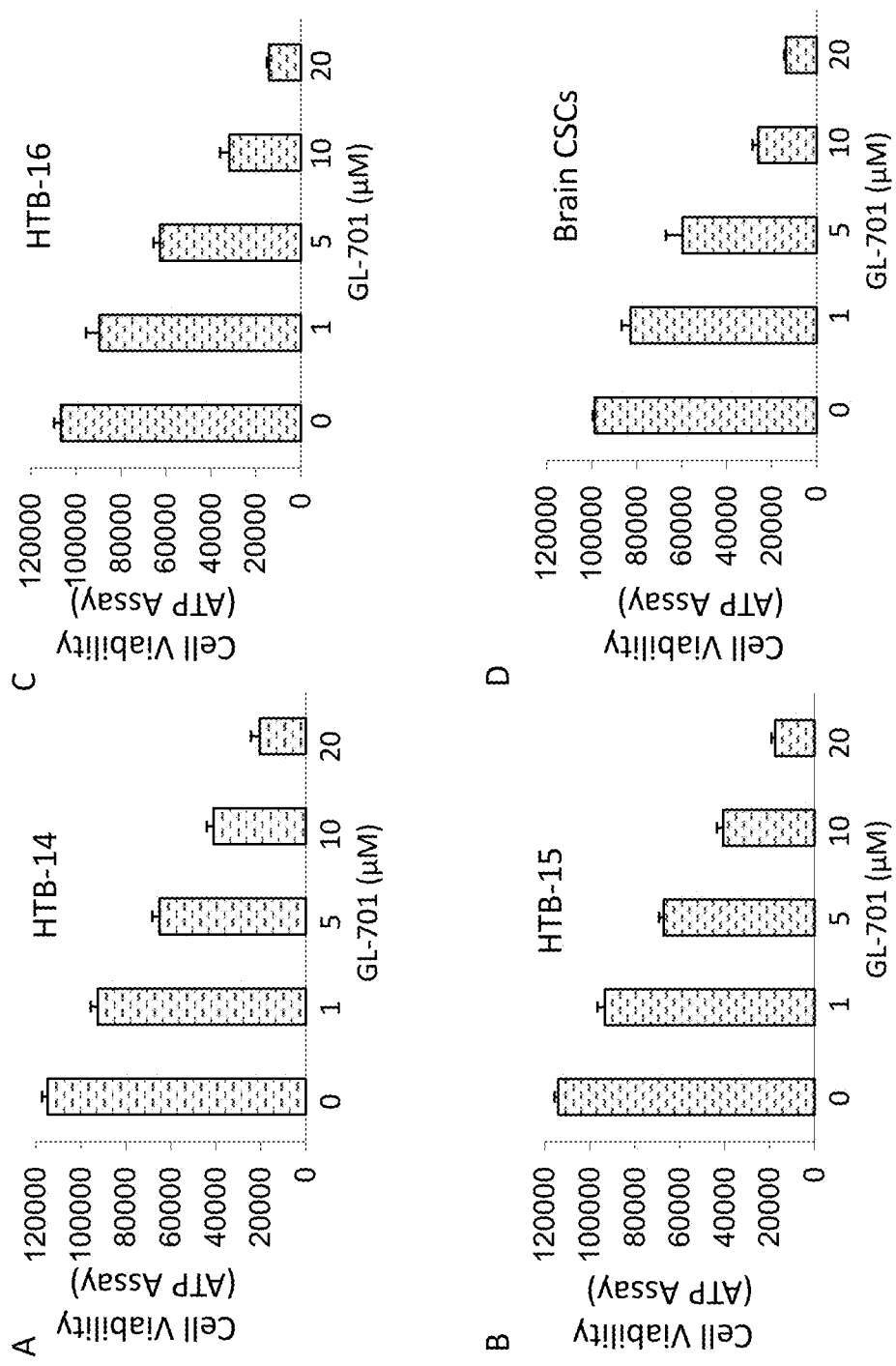
FIG. 15 shows GL-701 inhibits cell viability of human brain cancer cells and brain cancer stem cells.
Figure 16:
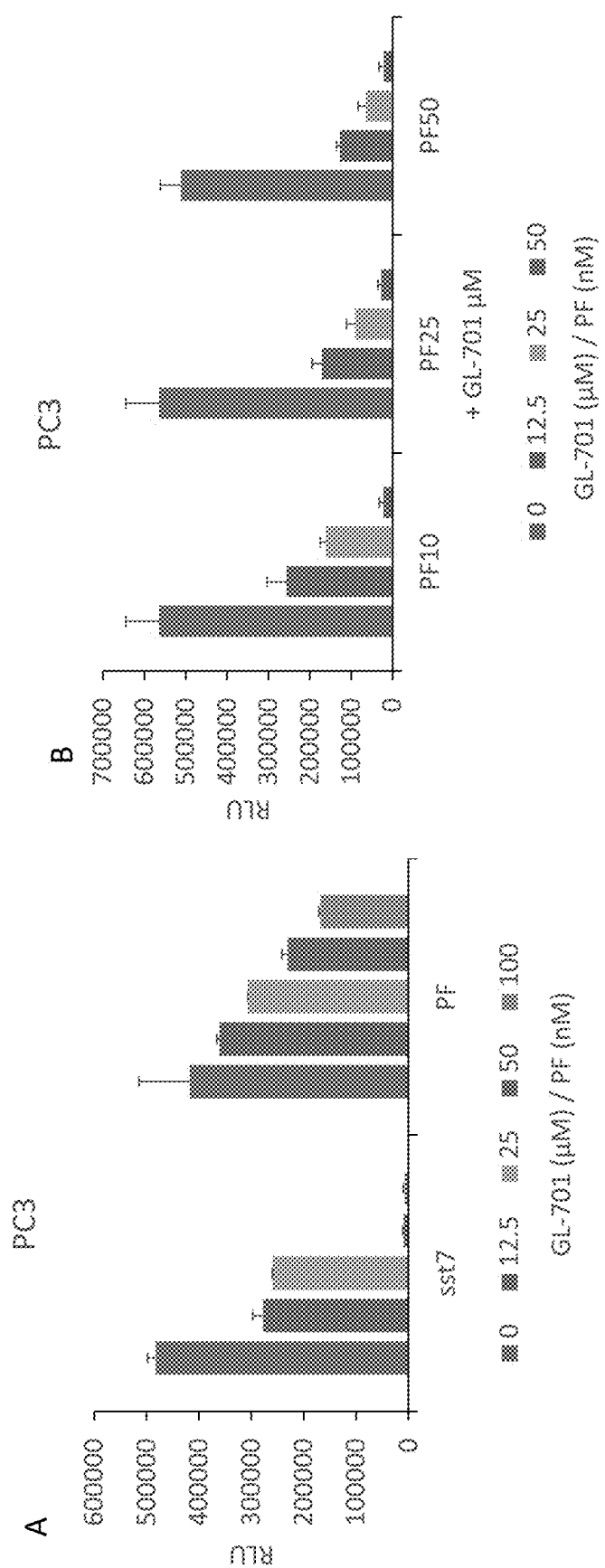
FIG. 16 shows that GL-701 co-operates with PF05212384 (PI3K/mTOR dual inhibitor) in inhibiting cell viability of human prostate cancer cells.

Molecular dynamics studies of Compound 8 on human smoothened 7TM receptor (PDB Code: 4JKV) protein showed the H-bonding interactions with Glh518 and Tyr394 remained intact and completely stable for the maximum period of simulation run (FIG. 10 and FIG. 11). The NH group of Compound 8 is making H-bonding contact with Glh518 and Tyr394 while the phenyl ring is showing π-π stacking interaction with Trp281 and cation-π interaction with Arg400. It also displays hydrophobic interaction with important amino acids Trp281, Phe391, and Phe484.

REFERENCES CITED IN THIS EXAMPLE

Mamelak, A. N. and D. B. Jacoby, Targeted delivery of antitumoral therapy to glioma and other malignancies with synthetic chlorotoxin (TM-601). Expert opinion on drug delivery, 2007. 4(2): p. 175-186.

Evangelista, M., H. Tian, and F. J. de Sauvage, The hedgehog signaling pathway in cancer. Clinical Cancer Research, 2006. 12(20): p. 5924-5928.

Tang, S. N., et al., Inhibition of sonic hedgehog pathway and pluripotency maintaining factors regulate human pancreatic cancer stem cell characteristics. International journal of cancer, 2012. 131(1): p. 30-40.

Wen, P. Y. and S. Kesari, Malignant gliomas in adults. New England Journal of Medicine, 2008. 359(5): p. 492-507.

Congreve, M., J. M. Dias, and F. H. Marshall, Structure-based drug design for G protein-coupled receptors, in Progress in medicinal chemistry. 2014, Elsevier. p. 1-63.

Sharma, D., et al., Synthesis, Src kinase inhibitory and anticancer activities of 1-substituted 3-(N-alkyl-N-phenylamino) propane-2-ols. Biochimie, 2010. 92(9): p. 1164-1172.

Meanwell, N. A., Synopsis of some recent tactical application of bioisosteres in drug design. Journal of medicinal chemistry, 2011. 54(8): p. 2529-2591.

Gautam, M. K., S. N. Sonal, and J. K. Priyanka, Pharmacological profile and pharmaceutical importance of substituted benzoxazoles: a comprehensive review. Inter J ChemTech Res, 2012. 4(2): p. 640-650.

Peukert, S. and K. Miller-Moslin, Small-molecule inhibitors of the hedgehog signaling pathway as cancer therapeutics. ChemMedChem, 2010. 5(4): p. 500-512.

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A compound represented by the structure of Formula I below:

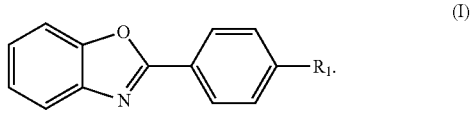

wherein $R_1$ is selected from

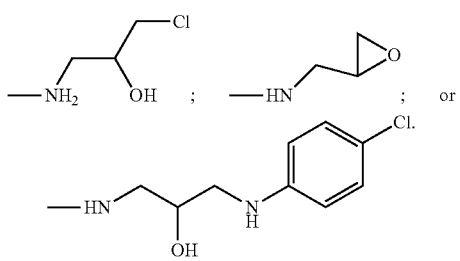

2. The compound of claim 1, comprising a $^1$H NMR spectral peak in the range of 3.231 to 3.335 ppm when $R_1$ is

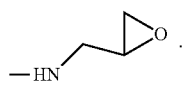

3. A pharmaceutical composition comprising the compound of claim 1 and a pharmaceutically acceptable carrier.

4. A method of treating a patient afflicted with cancer, the method comprising administering to the patient an effective amount of the compound of claim 1 and a pharmaceutically acceptable carrier.

5. The method of claim 4, wherein the cancer comprises glioma, glioblastoma, liver cancer, colorectal cancer, stomach cancer, brain cancer, prostate cancer, breast cancer, ovarian cancer, testicular cancer, gallbladder cancer, mesothelioma, kidney cancer, skin cancer, sarcoma, melanoma, retinoblastoma, skin cancer, head and neck cancer, thyroid cancer, vaginal cancer, leukemia, lymphoma, lung cancer, and pancreatic cancer.

6. The method of claim 4, wherein the compound is administered in a single dose.

7. The method of claim 4, wherein the compound is administered continuously.

8. The method of claim 4, wherein the compound is administered at intervals of about 4 hours, 12 hours, or 24 hours.

9. The method of claim 4, wherein the compound is administered orally, parentally, transdermally, or nasally.

10. A method of reducing cell viability, the method comprising contacting a cell with an effective amount of the compound of claim 1 and a pharmaceutically acceptable carrier.

11. A method of inducing apoptosis of a cell, the method comprising contacting a cell with an effective amount of the compound of claim 1 and a pharmaceutically acceptable carrier.

12. A method of inhibiting cell proliferation, the method comprising contacting a cell with an effective amount of the compound of claim 1 and a pharmaceutically acceptable carrier.

13. A method of regulating epithelial-mesenchymal transition (EMT), the method comprising contacting a cell with an effective amount of the compound of claim 1 and a pharmaceutically acceptable carrier.

14. A method of inhibiting tumor growth, the method comprising contacting a cell with an effective amount of the compound of claim 1 and a pharmaceutically acceptable carrier.

15. The method of claim 14, wherein tumor growth is inhibited by inducing cellular apoptosis and/or inhibiting cellular proliferation.

16. The method of any one of claims 10-14, wherein the cell comprises a cancer cell.

17. The method of claim 16, wherein the cancer cell comprises a glioma cancer cell, glioblastoma cancer cell, liver cancer cell, colorectal cancer cell, stomach cancer cell, brain cancer cell, prostate cancer cell, breast cancer cell, skin cancer, ovarian cancer cell, testicular cancer cell, gallbladder cancer cell, mesothelioma cancer cell, kidney cancer cell, sarcoma cancer cell, melanoma cancer cell, retinoblastoma cancer cell, skin cancer cell, head and neck cancer cell, thyroid cancer cell, vaginal cancer cell, leukemia cancer cell, lymphoma cancer cell, lung cancer cell, and pancreatic cancer cell.

18. The method of any one of claims 10-14, wherein the compound is administered to a subject prior to contacting.

19. A medical kit suitable for the treatment of cancer, comprising:
   printed instructions for administering the compound of claim 1 to a subject afflicted with a cancer; or
   the pharmaceutical composition comprising the compound of claim 1 and a pharmaceutically acceptable carrier.

20. The compound of claim 1, comprising a $^1$H NMR spectral peak in the range of 3.860 to 3.870 ppm when $R_1$

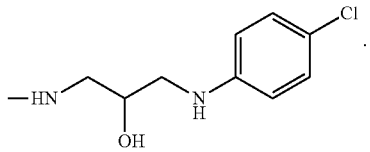

* * * * *